US011980740B2

(12) United States Patent
Howell et al.

(10) Patent No.: US 11,980,740 B2
(45) Date of Patent: May 14, 2024

(54) STABILIZATION AND GUIDE APPARATUS FOR ACCESS TO AN IMPLANTED ACCESS PORT AND RELATED METHODS

(71) Applicant: C. R. Bard, Inc., Franklin Lakes, NJ (US)

(72) Inventors: Glade H. Howell, Draper, UT (US); Bradley J. VanderStek, West Bountiful, UT (US); Jeremy B. Cox, Salt Lake City, UT (US); Laurie M. Whetstone, Magna, UT (US); Manikantan Shanmugham, Redmond, WA (US); Jason R. Stats, Layton, UT (US); Kenneth W. Sykes, Bluffdale, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 318 days.

(21) Appl. No.: 17/473,792

(22) Filed: Sep. 13, 2021

(65) Prior Publication Data

US 2021/0402085 A1 Dec. 30, 2021

Related U.S. Application Data

(62) Division of application No. 16/529,537, filed on Aug. 1, 2019, now Pat. No. 11,123,481, which is a division
(Continued)

(51) Int. Cl.
*A61M 5/158* (2006.01)
*A61M 39/02* (2006.01)

(52) U.S. Cl.
CPC ........ *A61M 5/158* (2013.01); *A61M 39/0208* (2013.01); *A61M 2005/1585* (2013.01); *A61M 2039/0238* (2013.01)

(58) Field of Classification Search
CPC .. A61M 2005/1585; A61M 2039/0238; A61M 39/0208; A61M 5/158
See application file for complete search history.

(56) References Cited

U.S. PATENT DOCUMENTS

| 5,061,248 A | 10/1991 | Sacco |
| 5,342,311 A | 8/1994 | Dirina |
(Continued)

FOREIGN PATENT DOCUMENTS

| CN | 1878591 A | 12/2006 |
| CN | 1899222 A | 1/2007 |
(Continued)

OTHER PUBLICATIONS

CN 201580012524.5 filed Sep. 7, 2016 Office Action dated Jan. 21, 2019.
(Continued)

*Primary Examiner* — Deanna K Hall
(74) *Attorney, Agent, or Firm* — Rutan & Tucker LLP

(57) ABSTRACT

An insertion device to assist in accessing an access port that has been subcutaneously implanted in the body of a patient is disclosed. The implanted access port is accessed by a needle of a needle assembly, such as a needle-based infusion set. The insertion device may include a body having a stabilizing portion and a guide portion. The stabilizing portion stabilizes a position of the implanted access port when the body is placed on the skin of the patient atop the implanted access port. The guide portion is designed to guide a needle of the needle assembly along a predetermined path such that the needle transcutaneously pierces a septum of the implanted access port.

15 Claims, 17 Drawing Sheets

Related U.S. Application Data of application No. 14/639,706, filed on Mar. 5, 2015, now Pat. No. 10,420,884.

(60) Provisional application No. 62/048,679, filed on Sep. 10, 2014, provisional application No. 61/949,972, filed on Mar. 7, 2014.

(56) References Cited

U.S. PATENT DOCUMENTS

| | | | |
|---|---|---|---|
| 5,360,407 A | 11/1994 | Leonard et al. | |
| 5,423,334 A | 6/1995 | Jordan | |
| 5,460,612 A | 10/1995 | Madore | |
| 5,476,460 A | 12/1995 | Montalvo | |
| 5,533,979 A | 7/1996 | Nabai et al. | |
| 5,620,419 A | 4/1997 | Lui et al. | |
| 5,758,667 A | 6/1998 | Slettenmark | |
| 5,771,895 A | 6/1998 | Slager | |
| 5,797,954 A | 8/1998 | Shaffer et al. | |
| 6,654,629 B2 | 11/2003 | Montegrande | |
| 6,673,091 B1 | 1/2004 | Shaffer et al. | |
| 7,044,932 B2 | 5/2006 | Borchard et al. | |
| 7,329,239 B2 | 2/2008 | Safabash et al. | |
| 7,621,749 B2 | 11/2009 | Munday | |
| 7,632,263 B2 | 12/2009 | Denoth et al. | |
| 7,708,730 B2 | 5/2010 | Steinbach et al. | |
| 7,762,993 B2 | 7/2010 | Perez | |
| 7,794,451 B1 | 9/2010 | Chuter et al. | |
| 7,824,371 B2 | 11/2010 | Perez | |
| 7,914,510 B2 | 3/2011 | Steinbach et al. | |
| 8,171,938 B2 | 5/2012 | Bengtson | |
| 8,177,808 B2 | 5/2012 | Mullani | |
| 8,192,398 B2 | 6/2012 | Hoendervoogt et al. | |
| 8,246,578 B2 | 8/2012 | Matsumoto | |
| 8,308,740 B2 | 11/2012 | Tolley et al. | |
| 8,475,407 B2 | 7/2013 | Kalpin et al. | |
| 8,534,293 B2 | 9/2013 | Bzostek et al. | |
| RE44,639 E | 12/2013 | Squitieri | |
| 8,715,232 B2 | 5/2014 | Yodfat et al. | |
| 8,795,229 B2 | 8/2014 | Bakhtyari-Nejad-Esfahani | |
| 8,894,616 B2 | 11/2014 | Harrison et al. | |
| 8,926,591 B2 | 1/2015 | Schutz et al. | |
| 8,974,422 B2 | 3/2015 | Gill et al. | |
| 9,884,150 B2 | 2/2018 | Jho et al. | |
| 10,420,884 B2 | 9/2019 | Howell et al. | |
| 10,471,205 B2 | 11/2019 | Jho et al. | |
| 2002/0022855 A1 | 2/2002 | Bobroff et al. | |
| 2002/0067359 A1 | 6/2002 | Brodsky et al. | |
| 2002/0072720 A1 | 6/2002 | Hague et al. | |
| 2003/0040753 A1 | 2/2003 | Daum et al. | |
| 2003/0163096 A1 | 8/2003 | Swenson et al. | |
| 2003/0204165 A1 | 10/2003 | Houben et al. | |
| 2005/0059884 A1 | 3/2005 | Krag | |
| 2005/0101912 A1 | 5/2005 | Faust et al. | |
| 2005/0119611 A1 | 6/2005 | Marano-Ford et al. | |
| 2005/0154303 A1 | 7/2005 | Walker et al. | |
| 2006/0033609 A1 | 2/2006 | Bridgelall | |
| 2006/0247584 A1 | 11/2006 | Sheetz et al. | |
| 2006/0264898 A1 | 11/2006 | Beasley et al. | |
| 2007/0078391 A1 | 4/2007 | Wortley et al. | |
| 2007/0191772 A1 | 8/2007 | Wojcik | |
| 2007/0238984 A1 | 10/2007 | Maschke et al. | |
| 2007/0282196 A1 | 12/2007 | Birk et al. | |
| 2008/0004642 A1 | 1/2008 | Birk et al. | |
| 2008/0021313 A1 | 1/2008 | Eidenschink et al. | |
| 2008/0083413 A1 | 4/2008 | Forsell | |
| 2008/0319414 A1 | 12/2008 | Yodfat et al. | |
| 2009/0062744 A1 | 3/2009 | Weilbacher et al. | |
| 2009/0082782 A1 | 3/2009 | Kalpin | |
| 2009/0093765 A1 | 4/2009 | Glenn | |
| 2009/0105688 A1 | 4/2009 | McIntyre al. | |
| 2009/0156928 A1 | 6/2009 | Evans et al. | |
| 2009/0227951 A1 | 9/2009 | Powers et al. | |
| 2010/0004597 A1 | 1/2010 | Gyrn et al. | |
| 2010/0010339 A1 | 1/2010 | Smith et al. | |
| 2010/0141454 A1 | 6/2010 | Bantin | |
| 2010/0204765 A1 | 8/2010 | Hall et al. | |
| 2010/0256594 A1 | 10/2010 | Kimmell et al. | |
| 2010/0298704 A1 | 11/2010 | Pelissier et al. | |
| 2011/0237935 A1 | 9/2011 | Kalpin et al. | |
| 2011/0275930 A1 | 11/2011 | Jho et al. | |
| 2012/0172711 A1 | 7/2012 | Kerr et al. | |
| 2012/0289819 A1 | 11/2012 | Snow | |
| 2013/0218085 A1 | 8/2013 | Knobloch | |
| 2014/0039452 A1 | 2/2014 | Bangera et al. | |
| 2014/0097303 A1 | 4/2014 | Lake | |
| 2014/0207110 A1 | 7/2014 | Jonas | |
| 2015/0250944 A1 | 9/2015 | Howell et al. | |
| 2017/0100598 A1 | 4/2017 | Gross et al. | |
| 2018/0154075 A1 | 6/2018 | Jho et al. | |
| 2019/0029760 A1 | 1/2019 | Nahman et al. | |
| 2019/0329015 A1 | 10/2019 | Kang | |
| 2019/0350672 A1 | 11/2019 | Smith et al. | |
| 2019/0351136 A1 | 11/2019 | Howell et al. | |
| 2020/0061288 A1 | 2/2020 | Jho et al. | |
| 2020/0069929 A1 | 3/2020 | Mason et al. | |
| 2020/0368513 A1 | 11/2020 | Amin | |

FOREIGN PATENT DOCUMENTS

| | | |
|---|---|---|
| CN | 101066480 A | 11/2007 |
| CN | 101500626 A | 8/2009 |
| CN | 101815550 A | 8/2010 |
| CN | 103327902 A | 9/2013 |
| CN | 103328021 A | 9/2013 |
| JP | H6-296633 A | 10/1994 |
| JP | 2004-283289 A | 10/2004 |
| JP | 2006-102360 A | 4/2006 |
| JP | 2008539025 A | 11/2008 |
| JP | 2013-531999 | 8/2013 |
| WO | 2006101993 A2 | 9/2006 |
| WO | 2006116438 A2 | 11/2006 |
| WO | 2010015001 A1 | 2/2010 |
| WO | 2011140379 A2 | 11/2011 |
| WO | 2012034085 A1 | 3/2012 |
| WO | 2013/152209 A1 | 10/2013 |
| WO | 2014155075 A1 | 10/2014 |
| WO | 2015134766 A1 | 9/2015 |
| WO | 2019147857 A1 | 8/2019 |
| WO | 2022115099 A1 | 6/2022 |

OTHER PUBLICATIONS

EP 15757893.1 filed Aug. 30, 2016 Extended European Search Report dated Dec. 21, 2016.

EP 15757893.1 filed Aug. 30, 2016 Office Action dated Feb. 20, 2019.

PCT/US2015/018999 filed Mar. 5, 2015 Search Report dated Jul. 28, 2015.

U.S. Appl. No. 14/639,706, filed Mar. 5, 2015 Final Office Action dated Apr. 27, 2018.

U.S. Appl. No. 14/639,706, filed Mar. 5, 2015 Final Office Action dated Jul. 6, 2017.

U.S. Appl. No. 14/639,706, filed Mar. 5, 2015 Non-Final Office Action dated Dec. 31, 2018.

U.S. Appl. No. 14/639,706, filed Mar. 5, 2015 Non-Final Office Action dated Feb. 17, 2017.

U.S. Appl. No. 14/639,706, filed Mar. 5, 2015 Notice of Allowance dated May 10, 2019.

CN 201180033387.5 filed Jan. 5, 2013 First Office Action dated Oct. 16, 2014.

CN 201180033387.5 filed Jan. 5, 2013 Second Office Action dated Apr. 13, 2015.

CN 201180033387.5 filed Jan. 5, 2013 Third Office Action dated Sep. 2, 2015.

CN 201610592317.8 filed Jul. 25, 2016 Office Action dated Feb. 24, 2018.

CN 201610592317.8 filed Jul. 25, 2016 Office Action dated Nov. 12, 2018.

JP 2013-509275 filed Oct. 30, 2012 Decision of Rejection dated Sep. 2, 2015.

(56) References Cited

OTHER PUBLICATIONS

JP 2013-509275 filed Oct. 30, 2012 First Office Action dated Feb. 6, 2015.
JP 2015-249575 filed Dec. 22, 2015 Decision for Rejection dated May 22, 2017.
JP 2015-249575 filed Dec. 22, 2015 First Office Action dated Oct. 4, 2016.
MX/a/2012/012802 filed Nov. 1, 2012 Office Action dated May 31, 2013.
MX/a/2012/012802 filed Nov. 1, 2012 Office Action dated Nov. 19, 2013.
PCT/US2011/035406 filed May 5, 2011 International Preliminary Report on Patentability dated Feb. 20, 2014.
PCT/US2011/035406 filed May 5, 2011 International Seach Report dated Dec. 16, 2011.
PCT/US2011/035406 filed May 5, 2011 Written Opinion dated Dec. 16, 2011.
PCT/US2019/015013 filed Jan. 24, 2019 International Preliminary Report on Patentability dated Jul. 28, 2020.
PCT/US2019/015013 filed Jan. 24, 2019 International Search Report and Written Opinion dated Jun. 20, 2019.
PCT/US2020/062076 filed Nov. 24, 2020 International Preliminary Report on Patentability dated Apr. 14, 2023.
PCT/US2020/062076 filed Nov. 24, 2020 International Search Report and Written Opinion dated Aug. 11, 2021.
U.S. Appl. No. 13/101,968, filed May 5, 2011 Decision on Appeal dated Jun. 26, 2017.
U.S. Appl. No. 13/101,968, filed May 5, 2011 Final Office Action dated Feb. 6, 2015.
U.S. Appl. No. 13/101,968, filed May 5, 2011 Final Office Action dated Oct. 24, 2013.
U.S. Appl. No. 13/101,968, filed May 5, 2011 Non-Final Office Action dated Apr. 24, 2013.
U.S. Appl. No. 13/101,968, filed May 5, 2011 Non-Final Office Action dated Sep. 11, 2014.
U.S. Appl. No. 13/101,968, filed May 5, 2011 Notice of Allowance dated Sep. 20, 2017.
U.S. Appl. No. 16/961,213, filed Jul. 9, 2020 Non-Final Office Action dated Jun. 1, 2023.
U.S. Appl. No. 15/887,675, filed Feb. 2, 2018 Advisory Action dated Mar. 29, 2019.
U.S. Appl. No. 15/887,675, filed Feb. 2, 2018 Final Office Action dated Jan. 17, 2019.
U.S. Appl. No. 15/887,675, filed Feb. 2, 2018 Non-Final Office Action dated Jun. 14, 2018.
U.S. Appl. No. 15/887,675, filed Feb. 2, 2018 Restriction Requirement dated Apr. 11, 2018.
U.S. Appl. No. 16/672,062, filed Nov. 1, 2019 Board Decision dated May 5, 2022.
U.S. Appl. No. 16/672,062, filed Nov. 1, 2019 Final Office Action dated Jan. 19, 2022.
U.S. Appl. No. 16/672,062, filed Nov. 1, 2019 Non-Final Office Action dated Sep. 20, 2021.
Website: Analog IC Tips, article: How do RFID tags and reader antennas work? https://www.analogictips.com/rfid-tag-and-reader-antennas/ date: May 2, 2017 (Year: 2017).

STABILIZATION AND GUIDE APPARATUS FOR ACCESS TO AN IMPLANTED ACCESS PORT AND RELATED METHODS

PRIORITY

This application is a division of U.S. patent application Ser. No. 16/529,537, filed Aug. 1, 2019, now U.S. Pat. No. 11,123,481, which is a division of U.S. patent application Ser. No. 14/639,706, filed Mar. 5, 2015, now U.S. Pat. No. 10,420,884, which claims the benefit of priority to U.S. Provisional Application No. 61/949,972, filed Mar. 7, 2014, and to U.S. Provisional Application No. 62/048,679, filed Sep. 10, 2014, each of which is incorporated by reference in its entirety into this application.

BRIEF SUMMARY

Briefly summarized, embodiments of the present invention are directed to an insertion device to assist in accessing an access port that has been subcutaneously implanted in the body of a patient. The implanted access port is accessed by a needle of a needle assembly, such as a needle-based infusion set. In one embodiment, the insertion device comprises a body that includes a stabilizing portion and a guide portion. The stabilizing portion stabilizes a position of the implanted access port when the body is placed on the skin of the patient atop the implanted access port. The guide portion guides a needle of the needle assembly along a predetermined path such that the needle transcutaneously pierces a septum of the implanted access port.

In another embodiment, the insertion device includes a housing that is placed on the skin of the patient over the location of the implanted port in a manner that prevents the port from undesirably moving about in the subcutaneous tissue pocket in which the port is disposed. Once the implanted port is stabilized in this manner, a needle guide component of the device can receive therein a needle of the needle assembly and guide the needle as it is advanced in a downward direction in such a way as to pierce the skin and accurately penetrate the septum of the implanted port until the needle establishes fluid communication with the port reservoir. Fluid infusion and/or aspiration can then occur. The needle can similarly be retracted from the implanted port by reversing the above process.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to an insertion device to assist in providing needle access to an access port that has been subcutaneously implanted in the body of a patient. The needle is included as part of a needle assembly, such as a port access needle, and provides a fluid conduit through which medicaments or other fluids can be provided to or removed from the implanted access port.

The insertion device disclosed herein includes a stabilizing portion that is placed on the skin over the subcutaneously implanted access port to prevent undesired movement of the access port within its subcutaneous pocket. The insertion device further includes a guidance portion that is employed to temporarily secure the needle assembly to the insertion device and to guide insertion of a distal portion of the needle into the septum of the implanted access port so as to provide fluid access to the reservoir of the access port. Once the needle of the needle assembly is suitably inserted into the access port, the insertion device can be removed from the needle assembly and the needle assembly can be dressed and used.

Figure 1A:
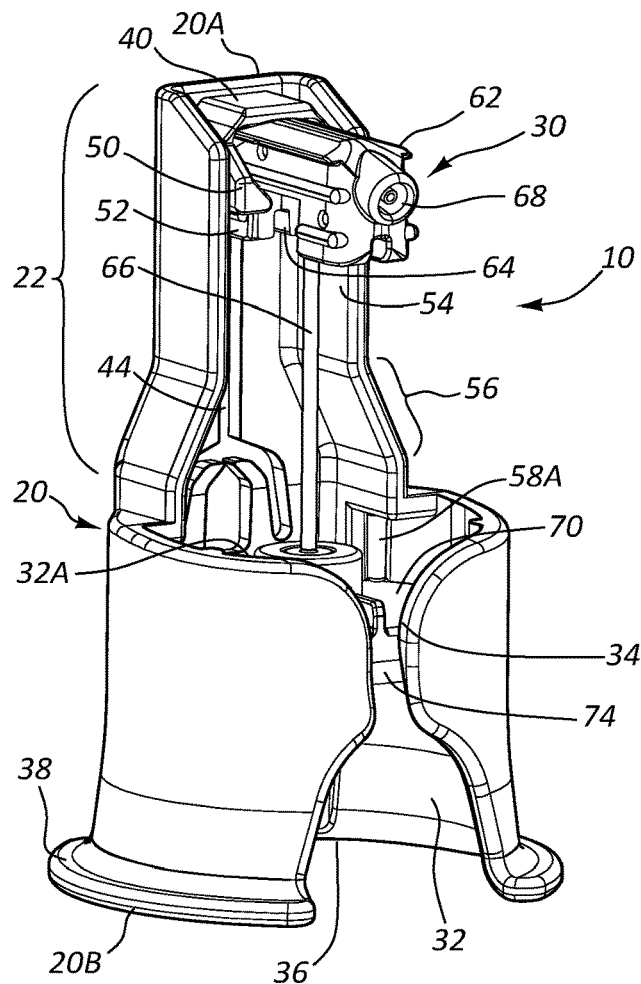
FIGS. 1A-1F are various views of an insertion device and needle assembly according to one embodiment.
Figure 1B:
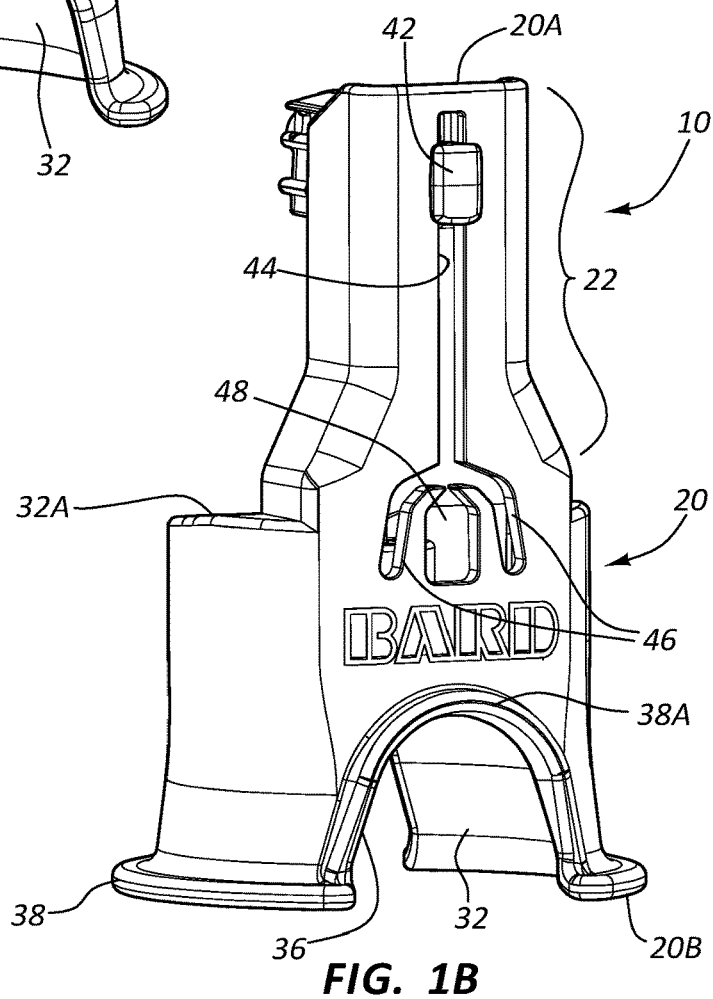

Reference is first made to FIGS. 1A-1F, which depict various views of a port needle insertion device ("insertion device"), generally designated at 10, for assisting in providing needle access to an access port that has been subcutaneously implanted into the body of a patient, according to one embodiment. As shown, the insertion device 10 includes a stabilization and guide body ("body") 20 extending between a proximal end 20A and a distal end 20B. A tower-like proximal portion 22 extends above the generally cylindrical lower portion of the insertion device 10, as seen in FIGS. 1A and 1B.

The lower portion of the insertion device 10 defines a generally cylindrical cavity 32, though other cavity shapes are contemplated. The cavity 32 is sized so as to receive therein a portion of a needle assembly 30 (FIGS. 3A, 3B), such as a port access needle, for instance, as will be described below. The needle assembly 30 is removably attached to the insertion device. A slot 34 is defined in the body 20 adjacent the cavity 32 so as to enable separation of the needle assembly 30 from the insertion device 10 after use thereof is no longer needed.

The insertion device body 20 defines oppositely-disposed, rounded finger cutouts 36 that open to the distal end 20B of the body and the cavity 32 and assist with grasping the skin about the implanted access port while using insertion device 10. The shape, size, and position of the finger cutouts can vary. A radially outward extending lip 38 is defined about the perimeter of the distal end 20B of the insertion device body 20 to assist with placement of the insertion device on the skin of the patient during use. The lip 38 extends between both finger cutouts 36. The distal end of the insertion device body 20 including the lip 38, as well as the cavity 32, cooperate to define a stabilization portion of the insertion device, according to one embodiment.

In the present embodiment, a lip extension 38A is also defined about the finger cutout 36 shown in FIG. 1B to help a user grasp the insertion device 10 during use.

Figure 3A:
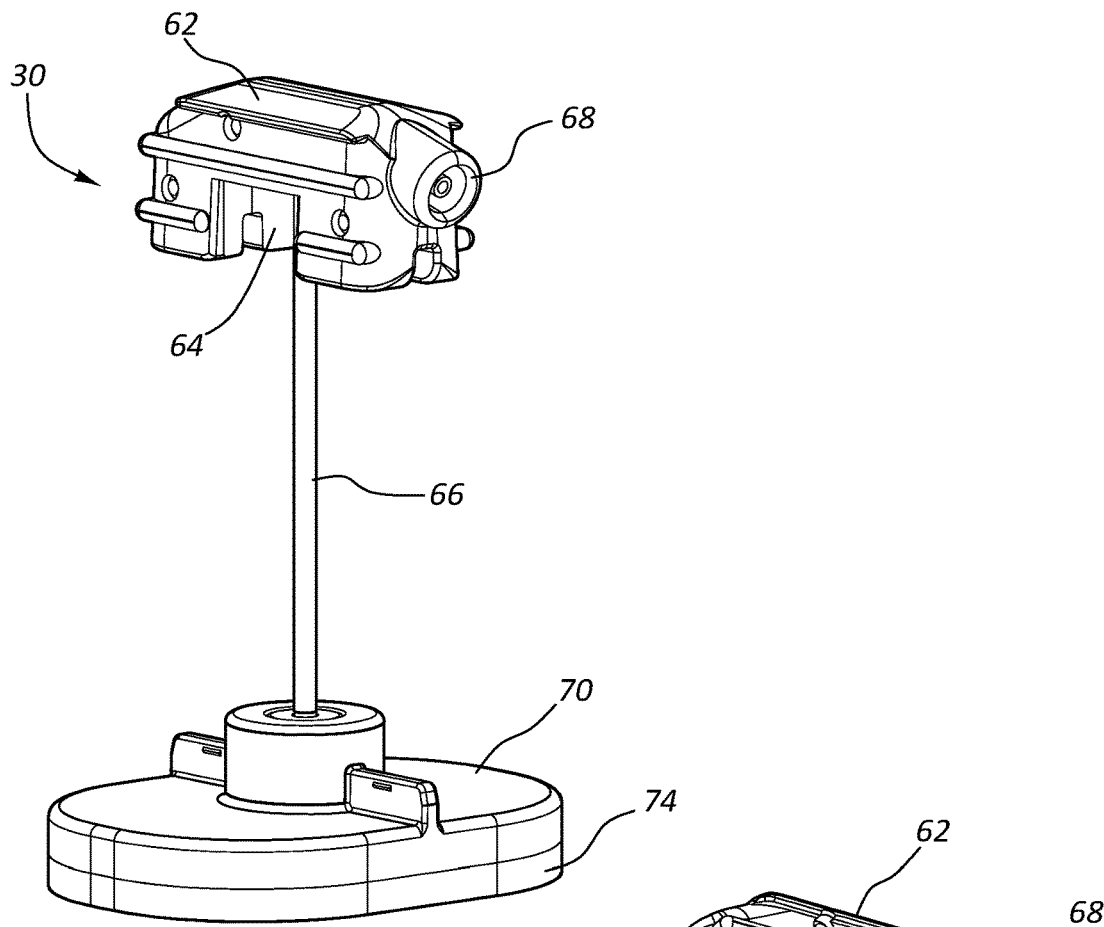
FIGS. 3A-3B show various views of the needle assembly of FIGS. 1A-1F.
Figure 3B:
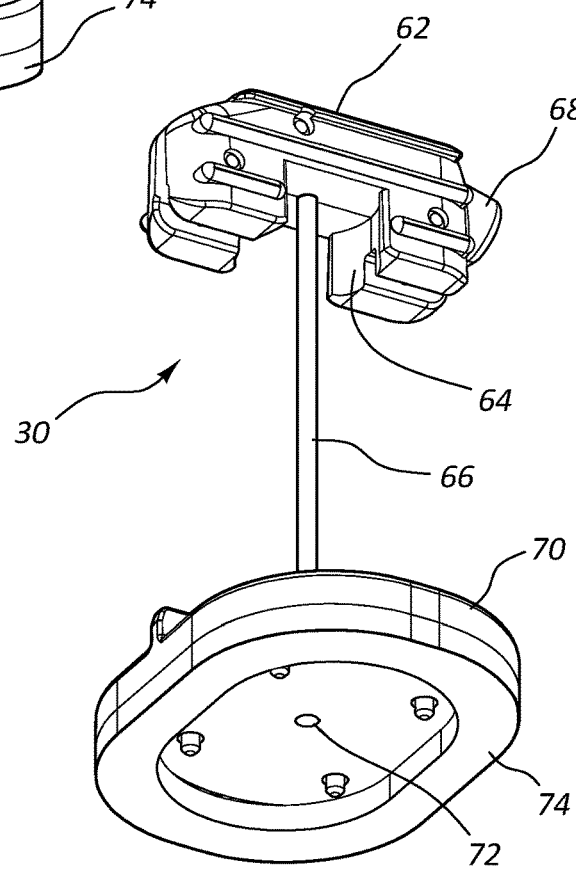

Reference is made to FIGS. 3A and 3B, which depict various details of the needle assembly 30 according to the present embodiment. As shown, the needle assembly 30 includes a hub 62 that defines a cavity 64 therein. A hollow needle 66 including an open distal tip 66A (FIG. 4B) is attached to the hub 62 and extends distally from the cavity 64. A fluid inlet 68 is included on the hub 62 and is in fluid communication with the needle 66. Tubing is typically connected to the fluid inlet 68.

The needle assembly 30 further includes a base 70 that is slidably disposed on the needle 66. A hole 72 is defined in the base to enable the needle 66 to extend therethrough. A pad 74 is attached to a bottom surface of the base 70. The base 70 is slidable along the needle 66 so as to be positioned adjacent the hub 62 such that a portion of the base is received into the cavity 64 and the distal tip 66A of the needle 66 extends through and beyond the hole 72. As shown in FIGS. 3A and 3B, the base 70 can also be extended distally from the hub 62. A safety mechanism is included in the base 70 so as to lock the base over the distal tip 66A of the needle 66 to prevent contact therewith when the base is distally extended a sufficient amount.

A retainer component, such as a needle hub retainer 40, is included with the insertion device 10 to retain the needle assembly 30 and to guide a needle 66 thereof into a septum of the subcutaneously implanted access port. As shown, the needle hub retainer 40 includes a projection 42 that extends through a slit 44 longitudinally defined in the proximal portion 22 of the body 20. This enables the needle hub retainer 40 to slide proximally and distally along the proximal portion of the body 20.

The above-referenced slit 44 is in communication with a hole 48 defined partly by two spring arms 46, best seen in FIG. 1B. During initial assembly of the insertion device, the projection 42 of the needle hub retainer 40 is inserted through the hole 48, then slid proximally toward the proximal end 20A of the body 20. This causes the spring arms 46 to flex outward to enable the projection 42 to pass between the spring arms, assisted by the proximally-angled arm surfaces. Once the projection has passed them, the spring arms 46 return to their positions shown in FIG. 1B, thus preventing the projection from re-entering the hole 48. In addition to this, other schemes for attachment of the needle hub retainer 40 to the body 20 are contemplated, as are differing designs for the needle hub retainer itself, such as in the case of accommodating other needle assembly designs.

Figure 1C:
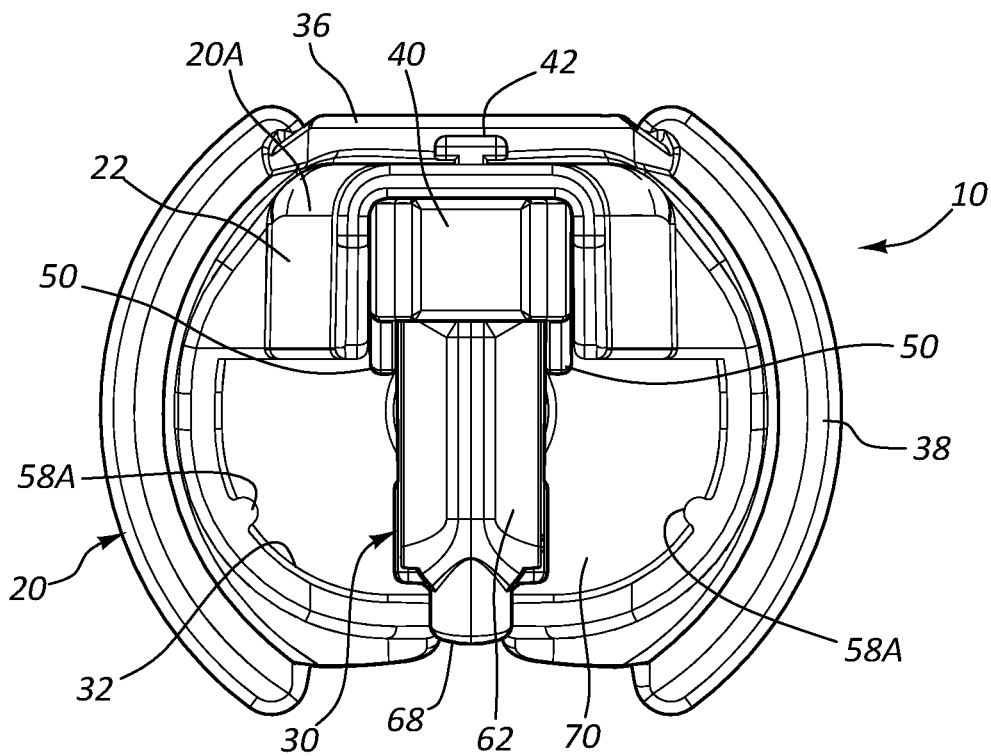
Figure 1D:
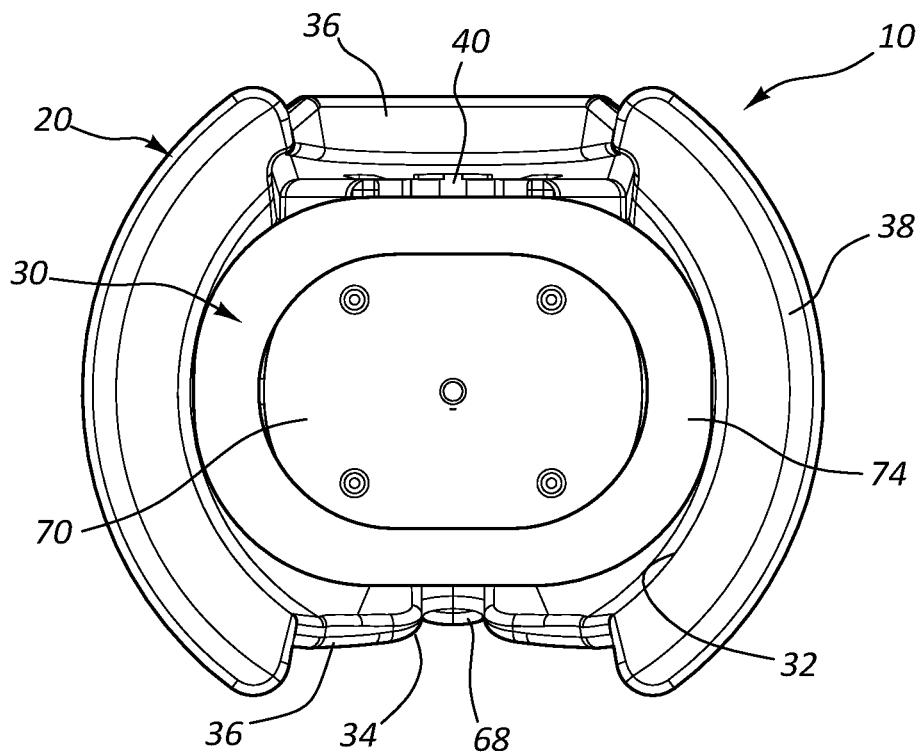
Figures 1E, 1F:
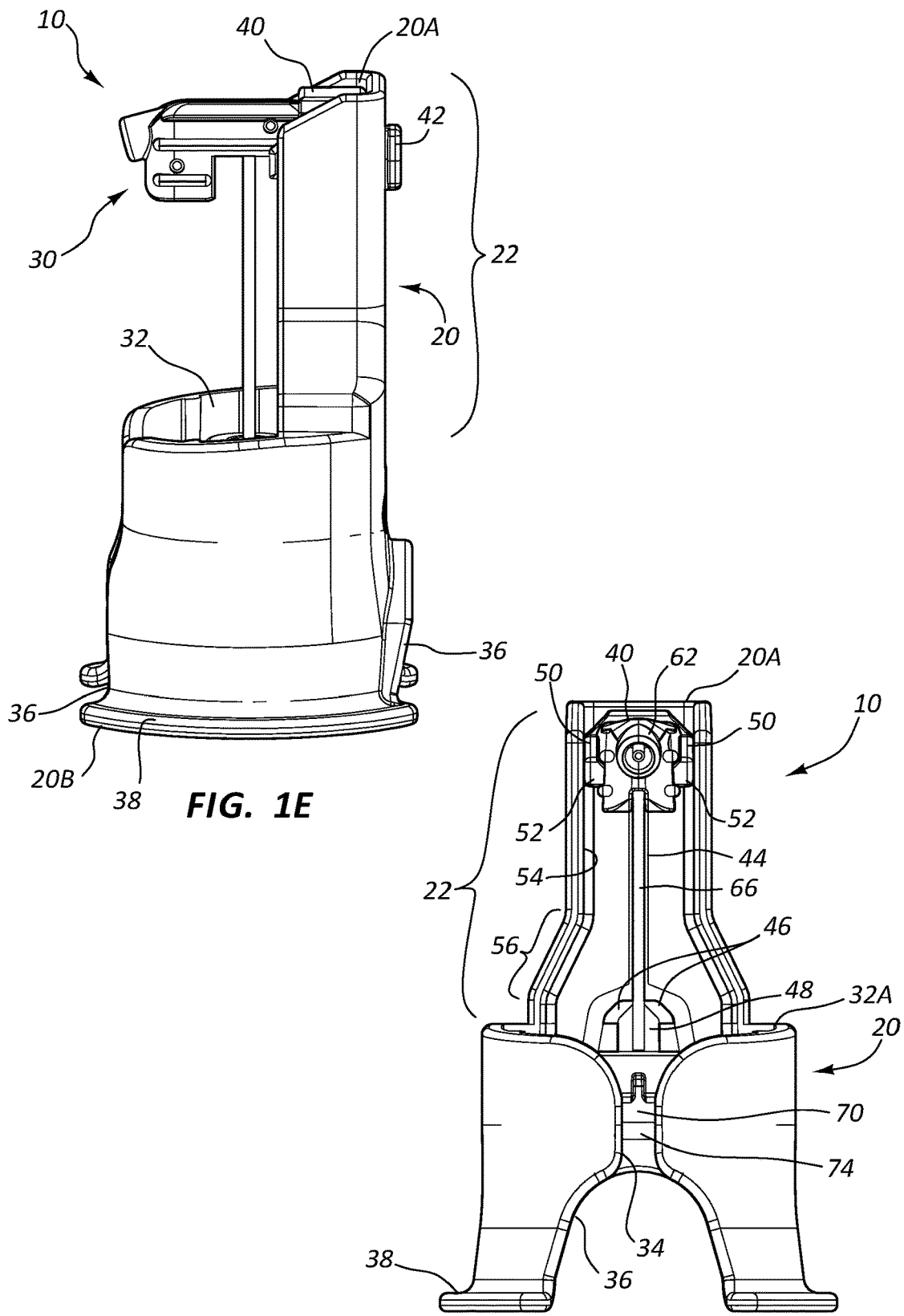
Figure 2A:
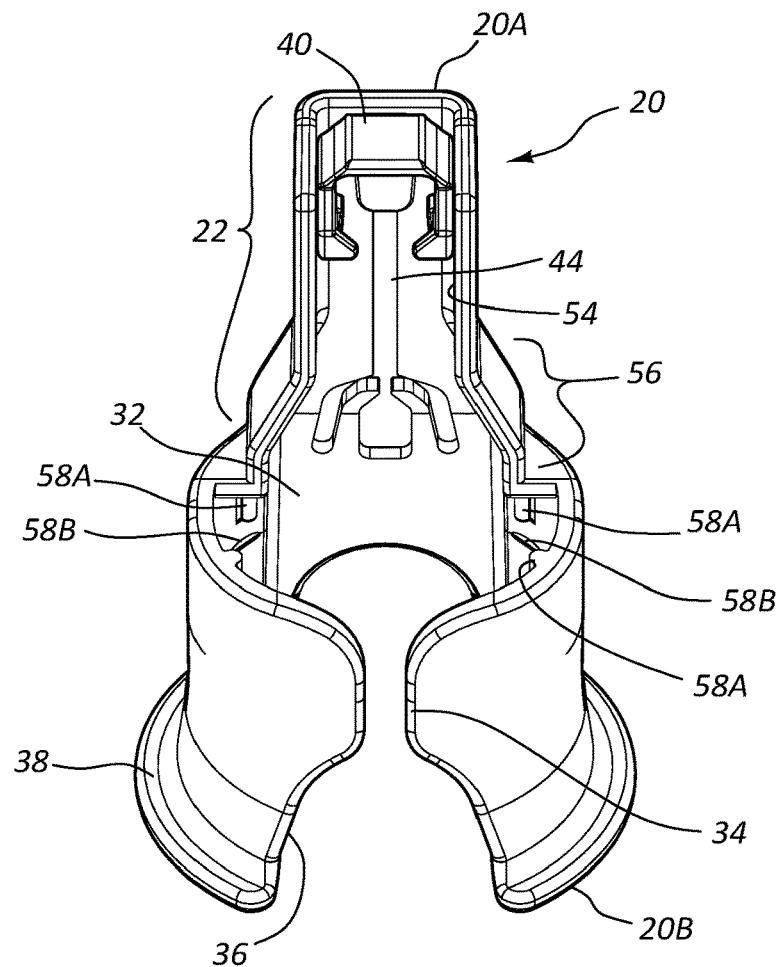
FIGS. 2A-2C show various views of the insertion device of FIGS. 1A-1F.
Figure 2B:
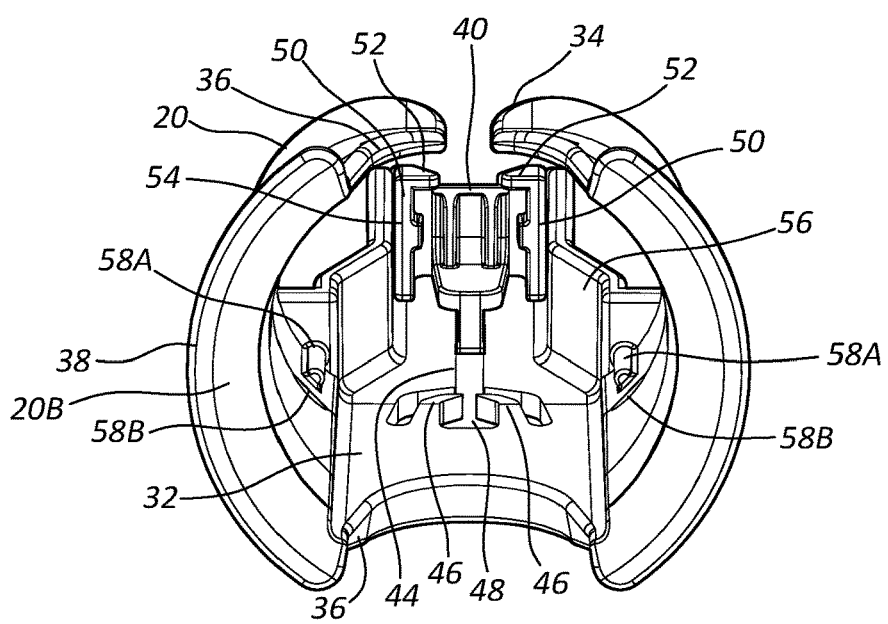
Figure 2C:
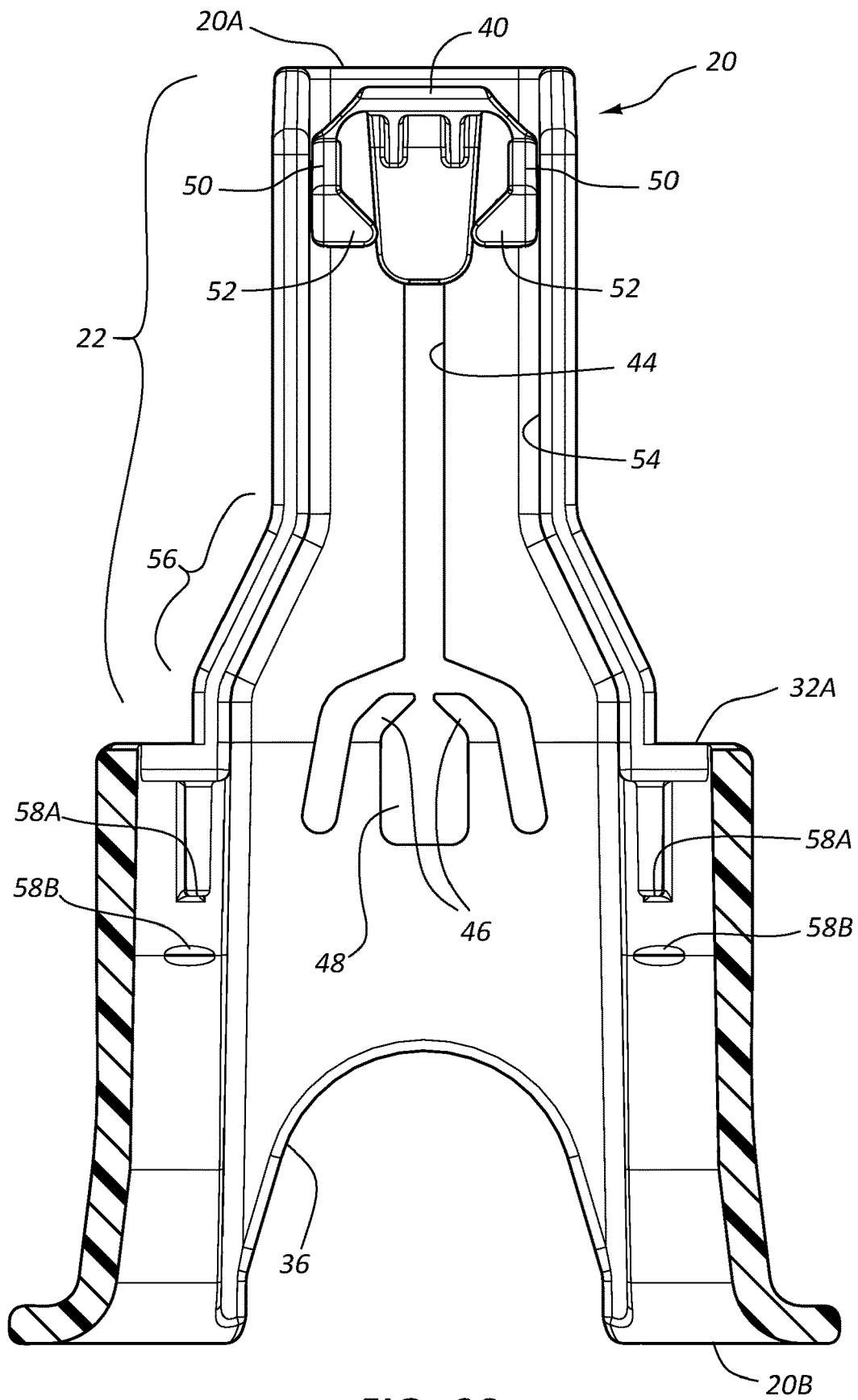

FIGS. 1E, 1F, 2A, and 2B show that the needle hub retainer 40 further includes two articulating wings 50, with each wing including a tooth 52. FIGS. 1E and 1F show that the teeth 52 and wings 50 are employed to fold about and capture the hub 62 of the needle assembly 30 (FIGS. 3A, 3B) so as to restrain travel of the hub while the needle assembly is attached to the insertion device 10. In particular, the teeth 52 are configured to engage the cavity 64 defined in the hub 62 of the needle assembly 30 so as to create a secure engagement between the needle hub and the needle hub retainer 40 when in the proximal position as shown in FIGS. 2C and 4A.

The needle hub retainer 40 is disposed in a longitudinal channel 54 defined by the proximal portion 22 of the body 20. Disposal of the projection 42 in the slit 44 keeps the needle hub retainer within the channel 54. The channel 54 includes parallel sides in a more proximal region that taper away from each other in a more distal tapered region 56 as the channel approaches the lower portion of the body 20. The needle hub retainer can travel distally until the projection 42 contacts the tops of the spring arms 46. So configured, it is appreciated that the needle hub retainer 40 and the channel 54 can guide movement of the needle assembly 30, as will be described below, and thus serve as a guide portion of the insertion device 10 in the present embodiment.

Figure 4A:
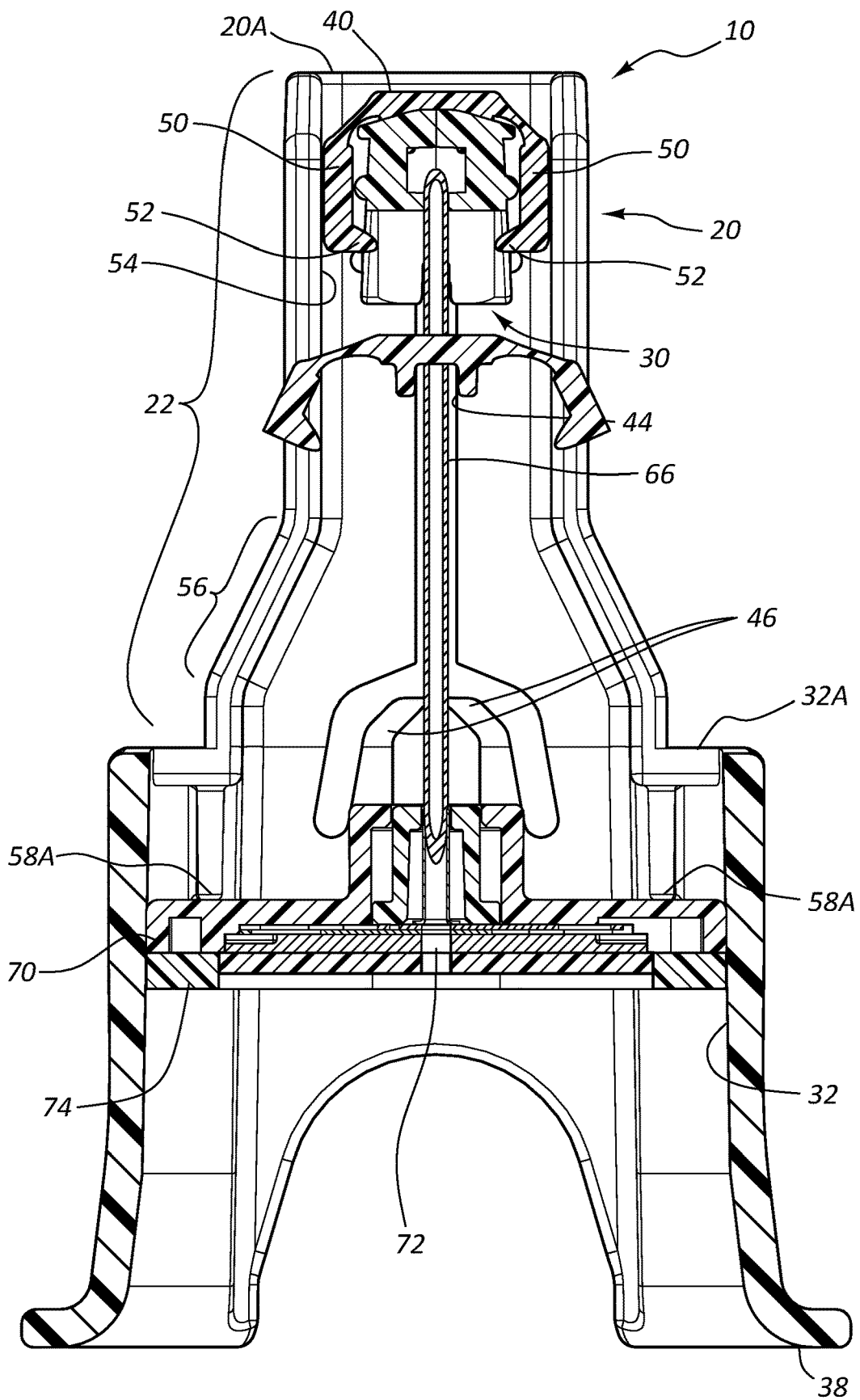
FIGS. 4A-4C show various stages of use of the insertion device of FIGS. 1A-1F.
Figure 4B:
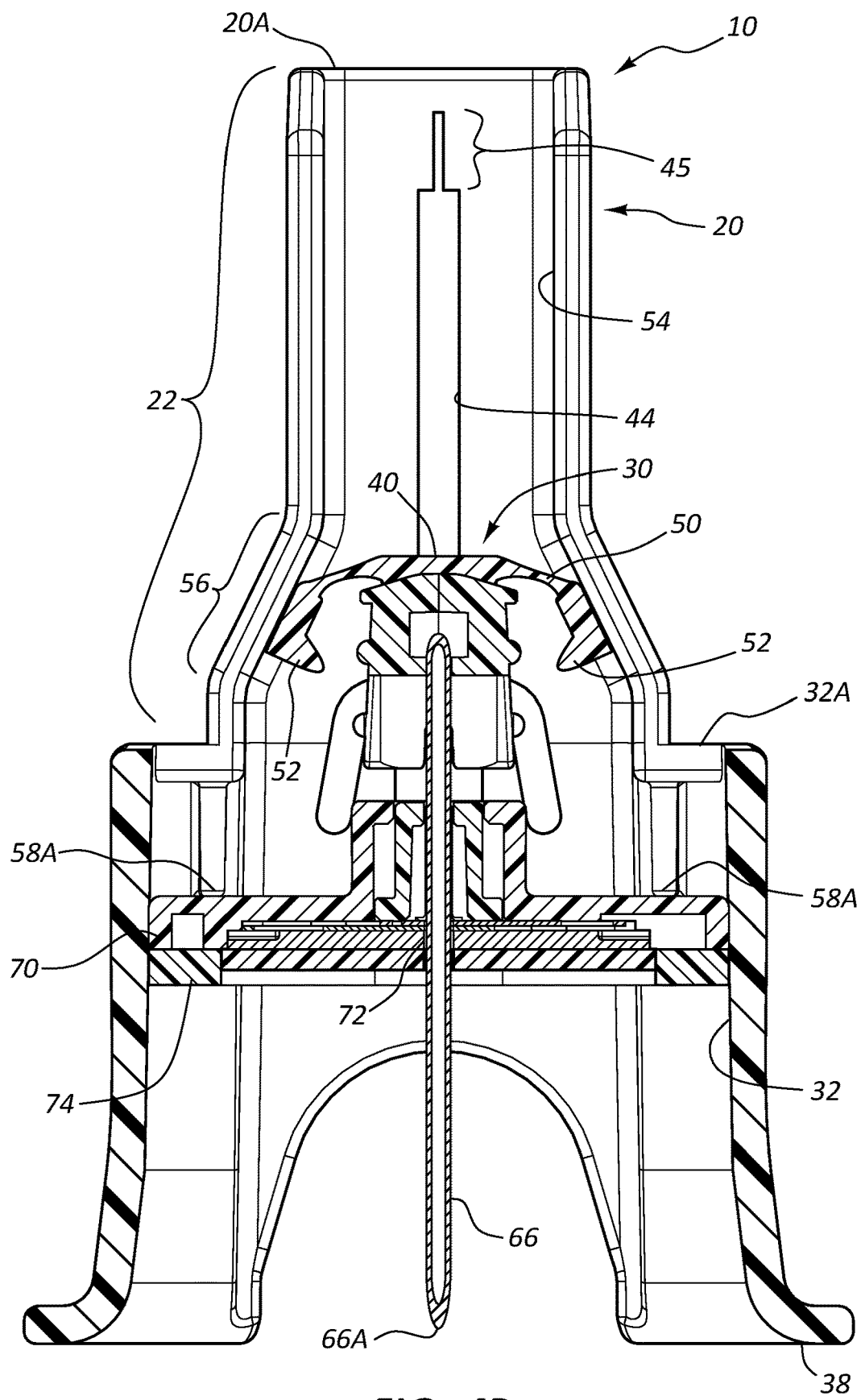
Figure 4C:
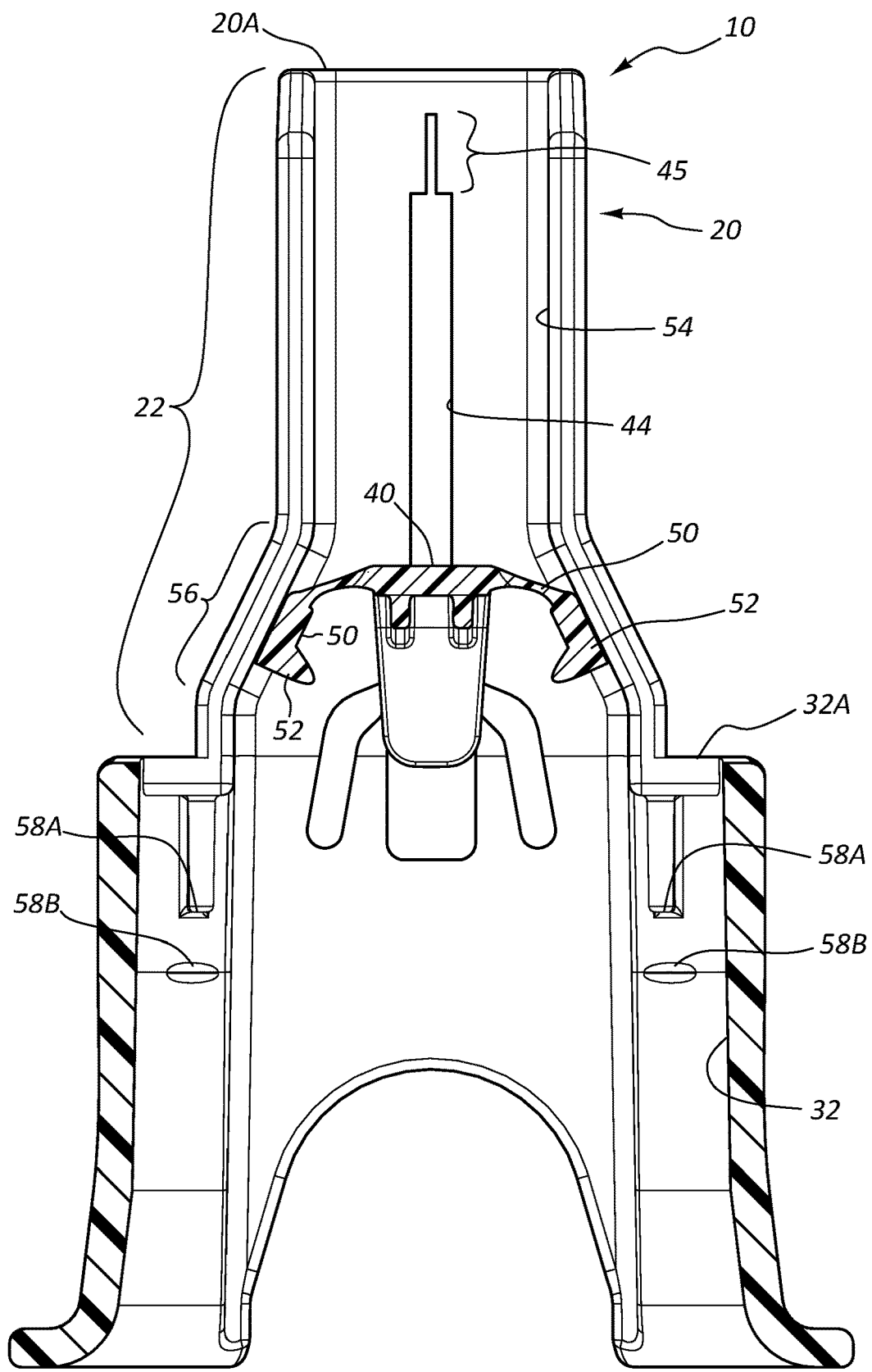

FIGS. 4A-4C depict the manner in which the needle assembly 30 is disposed in the insertion device and the nature of needle assembly movement therewithin. In particular, FIG. 4A shows the needle assembly 30 attached within the insertion device 10 such that the needle hub 62 is captured by the needle hub retainer 40 in the manner described above, and the base 70 is disposed in the cavity 32 of the body 20. FIGS. 1C and 2B show that four upper retention surfaces 58A and four corresponding lower retention surfaces 58B cooperate to sandwich the base 70 of the needle assembly and maintain it in place within the cavity 32. Of course, other retention modes could be employed.

FIG. 4B shows that a proximal portion of the slit 44 includes a slit adjustment zone 45. In one embodiment, during manufacture of the insertion device body 20 detail measurement of the length of the needle 66 are taken and the slit 44 can be lengthened as necessary by widening the slit adjustment zone to compensate for slight variations in the needle length, which can change from needle to needle. A punch-out tool or other device can be used to lengthen the slit 44 in the slit adjustment zone 45. Such adjustment enable the distal tip 66A of the needle to reside (before insertion device use) within the base 70 of the needle assembly 30 but distal to the safety assembly included in the base so as to enable the distal tip to emerge therefrom when extended distally to engage the septum of the implanted access port. Of course, other modes for extending the slit length can also be devised.

In the position shown in FIG. 4A, the insertion device 10 is ready to be placed on the patient's skin atop a subcutaneously implanted port in preparation for inserting the needle 66 of the needle assembly 30 into the port. In particular, the distal end 20B of the insertion device body 20 including the lip 38 is placed on the skin such that the perimeter defined by the distal end 20B circumscribes the implanted port. Some downward pressure on the insertion device body 20 may be used such that a portion of the skin-covered implanted port is raised into the cavity 32. This stabilizes the position of the implanted access port and prevents it from sliding, rotating, or otherwise undesirably moving during the needle insertion procedure. Further, placement of the insertion device 10 over the implanted access port centers the port in the cavity of 32 of the body 20, thus aligning the septum of the port with the needle 66 of the needle assembly 30 attached to the insertion device, so as to ensure accurate mating of the needle with the port, as described further below. Note that in other embodiments the size and cross-sectional shape of the cavity 32 can vary from the generally round configuration discussed here. For instance, the cross-sectional shape can be triangular, square, etc., in one embodiment.

Once the position of the implanted access port is stabilized, downward (distal) force can be applied to the needle hub 62, which causes the distal movement of the needle hub retainer 40, which is securely attached to the needle hub. Given the disposal of its projection 42 within the slit 44, the needle hub retainer 40 is constrained in its movement to a predetermined, substantially vertical (distal), path. Because of its attachment to the needle hub retainer 40, the needle hub 62 is likewise restricted in its movement in the same predetermined, vertical (distal) path. "Predetermined path," as used herein, includes passage of the needle along a desired path that leads to a septum of an implanted port or other desired subcutaneous target. The distally downward movement of the needle hub retainer 40 and needle hub 62 causes the corresponding distal movement of the distal tip 66A of the needle 66 from beyond the hole 72 of the base 70 and past the distal end 20B of the insertion device body 20, as shown in FIG. 4B.

Distal advancement of the needle 66 as just described in turn causes the distal tip 66A of the needle to penetrate the patient skin and pierce the septum of the implanted access port. Such insertion of the needle distal tip 66A is facilitated by the stabilizing and centering function of the implanted access port by the insertion device 10 as described above, desirably easing mating of the needle to the port by the clinician. During the needle insertion procedure, one hand of the clinician can be used to hold the insertion device body 20 (using the finger cutouts 36 for a thumb and finger, for example) against the patient skin to stabilize the implanted access port, while the other hand is used to apply downward pressure to the needle hub 62 to distally advance the needle 66 into the port.

FIG. 4B shows that distal advancement of the needle hub 62 (and, correspondingly, the needle 66), as constrained by the needle hub retainer 40, causes the needle hub retainer to slide distally down the channel 54 and into the outwardly tapered region 56 thereof. This in turn enables the living-hinged wings 50 to spread outwardly, which causes the teeth 52 to disengage from the cavity 64 of the needle hub 62. This frees the needle hub 62 from physical engagement with the needle hub retainer.

In light of the above disengagement of the needle hub retainer 40 from the needle hub 62, once the needle 66 has been acceptably inserted into the implanted access port, the insertion device 10 can be removed from the needle assembly 30 by lifting the insertion device vertically from the patient's skin surface. Compliance of the insertion device body 20 enables sufficient deformation for the needle assembly base 70 to free itself from retention by the lower retention surfaces 58B. As the insertion device is lifted from the patient's skin and past the inserted needle assembly 30, the tubing typically attached to the fluid inlet 68 of the needle hub 62 can pass through the slot 34 of the insertion device body 20, thus enabling full removal of the insertion device from the needle assembly. After its removal, the insertion device will appear substantially as shown in FIG. 4C.

It is appreciated that the insertion device can be modified so as to accommodate other types, sizes, and configurations of needle assemblies such that the stabilization and guide functions of the insertion device can be realized for other needle assemblies.

Figure 14:
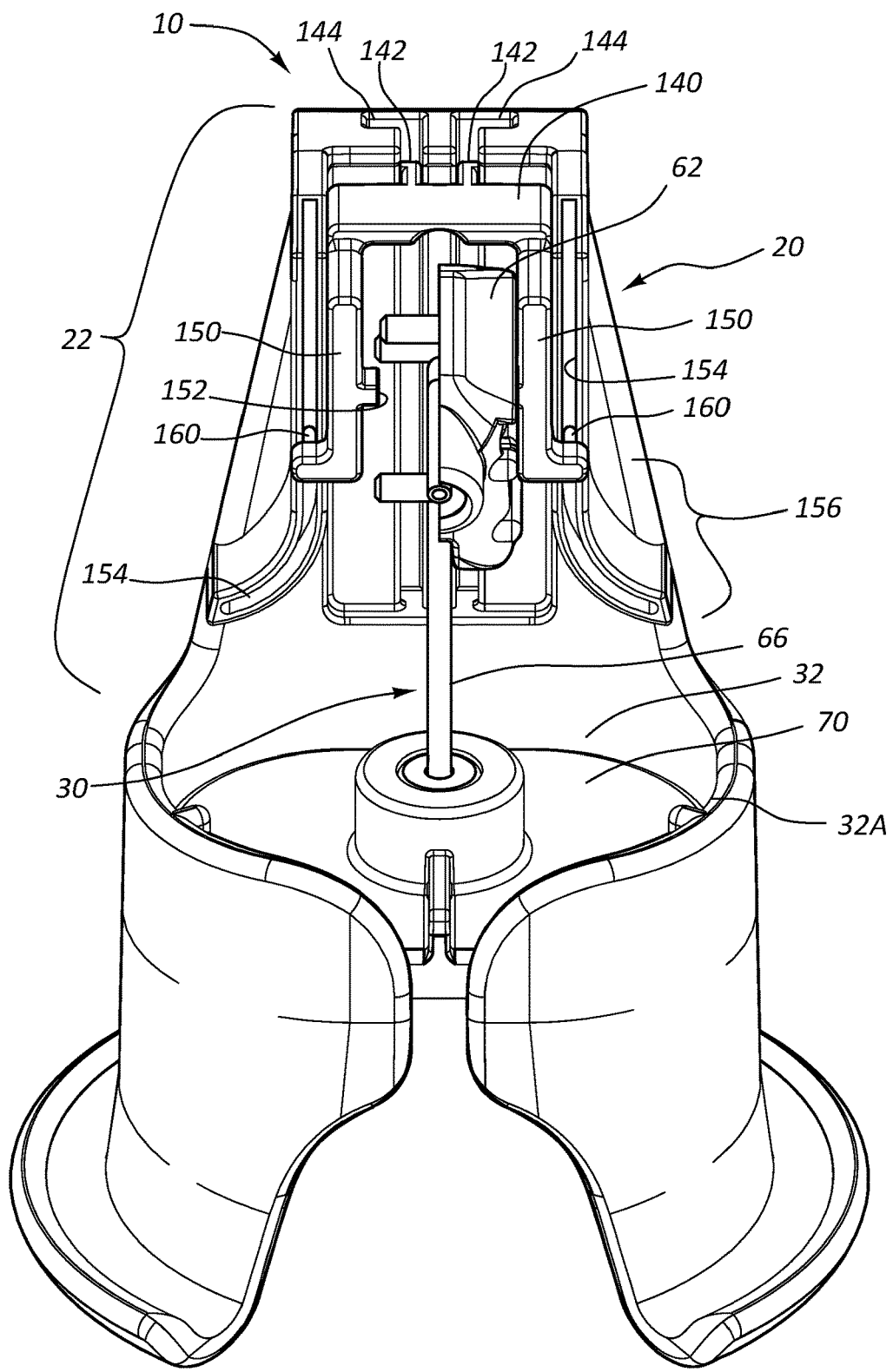
FIG. 14 is a perspective view of an insertion device according to one embodiment.

FIG. 14 depicts details of the insertion device 10 including a needle hub retainer according to another embodiment. As shown, the proximal portion 22 of the insertion device body 20 includes attached thereto a needle hub retainer 140 for releasably retaining the needle hub 62 of the needle assembly 30. The needle hub retainer 140 is slidably attached to the body 20 via two projections 142 that are slidably received into two corresponding grooves 144.

The needle hub retainer 140 includes two living-hinged wings 150 that each include one of two teeth 152 that serve to engage with hub portions surrounding a cavity defined by the needle hub 62 (a portion of the needle hub 62 is hidden here for clarity) to maintain attachment of the needle hub retainer 140 with the needle hub 62. Each wing 150 includes a pin that is slidably received within a corresponding one of two channels 154, as shown. The channels 154 each include a diverging region 156 that diverges outward from a more proximal parallel portion of the channel. Thus, as the needle hub retainer 140—initially retaining the needle hub 62—is slide distally down toward the cavity 32, the wings 150 are spread outward due to the tracking of the pins 160 within the corresponding diverging regions 156 of the channels 154. This causes the teeth 152 to release from engagement with the needle hub 62, which enables the needle hub to separate from the needle hub retainer 140 when separation of the insertion device 10 from the needle assembly 30 is desired after insertion of the needle 66 into the implanted access port. This and other variations of the needle hub retainer are therefore contemplated.

Note that, in one embodiment, the insertion device body 20 can include a pair of snap arms that can be used to removably retain tubing of the needle assembly 30.

Figure 5:
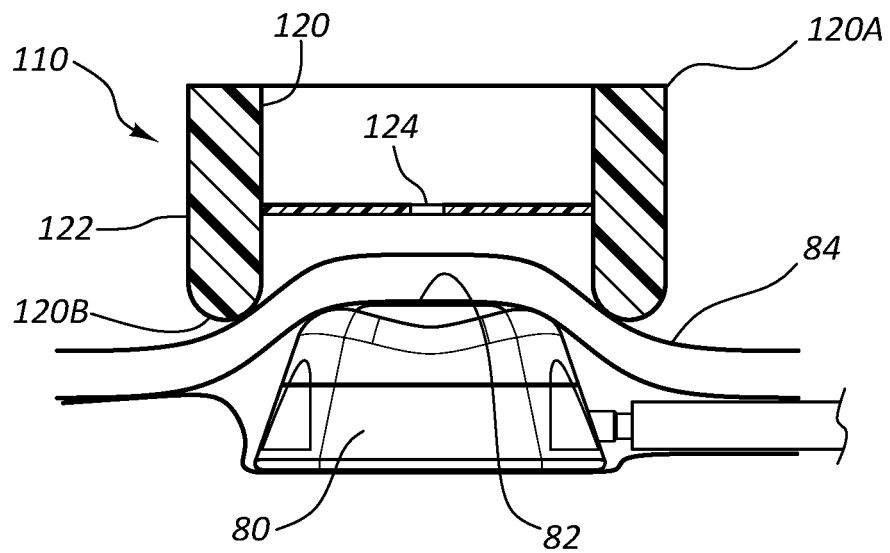
FIG. 5 is a cross-sectional side view of an insertion device according to one embodiment.

FIG. 5 shows a port needle insertion device ("insertion device") 110 according to another embodiment, wherein the insertion device includes a round body 120 extending between a proximal end 120A and a distal end 120B. The body 120 defines an annular rim 122 that circumscribes a removable, disk-like barrier 126. The barrier 126 defines a hole 124 to serve as a conduit through which a needle can be advanced. The barrier 126 in one embodiment includes foam or other suitable material that includes a useful component, such as an antimicrobial agent, a hemostatic agent, or both, for instance. In one embodiment, the barrier 126 is a GUARDIVA® Antimicrobial Hemostatic Dressing ("GUARDIVA® dressing") sold by Bard Access Systems, Salt Lake City, Utah, USA. Such a GUARDIVA® dressing can also be included with the insertion device described and shown in connection with the embodiment of FIGS. 1A-4C, in one embodiment, and with the other embodiments described herein.

The insertion device 110 is shown in FIG. 5 placed over a subcutaneously implanted access port 80 under the skin 84 of the patient so as to stabilize the position of the port via downward pressure of the annular rim 122 and to align the port with the hole 124 so that a needle passed through and guided by the hole along a predetermined path can intercept a septum 82 of the port, as desired. Being removable from the insertion device 110, the barrier 126 can be left interposed between the needle assembly 30 and the patient skin 84 after insertion of the needle 66 into the septum 82 of the implanted access port 80. In another embodiment, no barrier is included with the insertion device 110.

Figure 6:
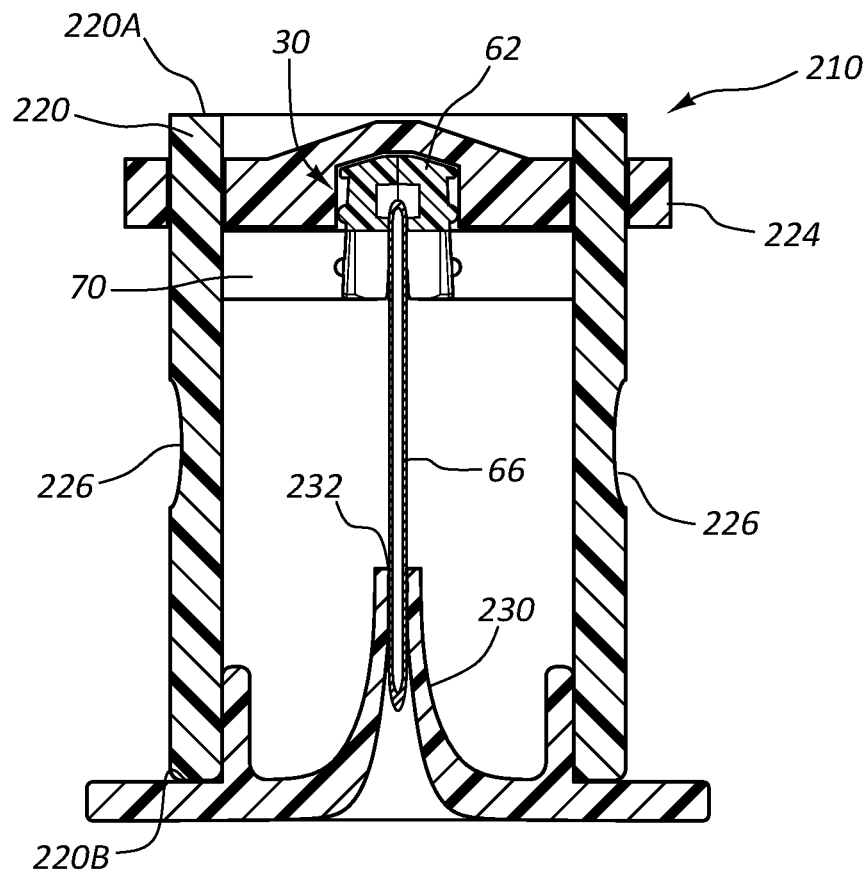
FIG. 6 is a cross-sectional side view of an insertion device according to one embodiment.

FIG. 6 shows a port needle insertion device ("insertion device") 210 according to another embodiment, wherein the insertion device includes a hollow cylindrical body 220 extending between a proximal end 220A and a distal end 220B. The insertion device 210 includes a slide portion 224 slidably mounted to the body 220, which removably supports the hub 62 of the needle assembly 30, similar to the needle assembly discussed in connection the embodiment of FIGS. 1A-4C. The slide portion 224 is distally slidable to distally advance the needle into an implanted access port stabilized by the distal end of the insertion device body 220. A needle cover 230 is shown in FIG. 6 removably attached to the distal end 220B of the insertion device body 220 and is used to protect the distal tip of the needle 66, but is removed prior to use of the insertion device 210.

As mentioned, the distal end of the insertion device body 220 serves as a stabilization portion for stabilizing the implanted access port when the insertion device 210 is placed over the implanted port. The slide 224 serves as a guide portion for guiding the needle along a predetermined path into the septum of the stabilized, implanted port, as desired. A longitudinal slot can be included in the insertion device body to enable detachment of the insertion device 210 from the needle assembly 30 after insertion of the needle 66 into the implanted access port.

Figure 7:
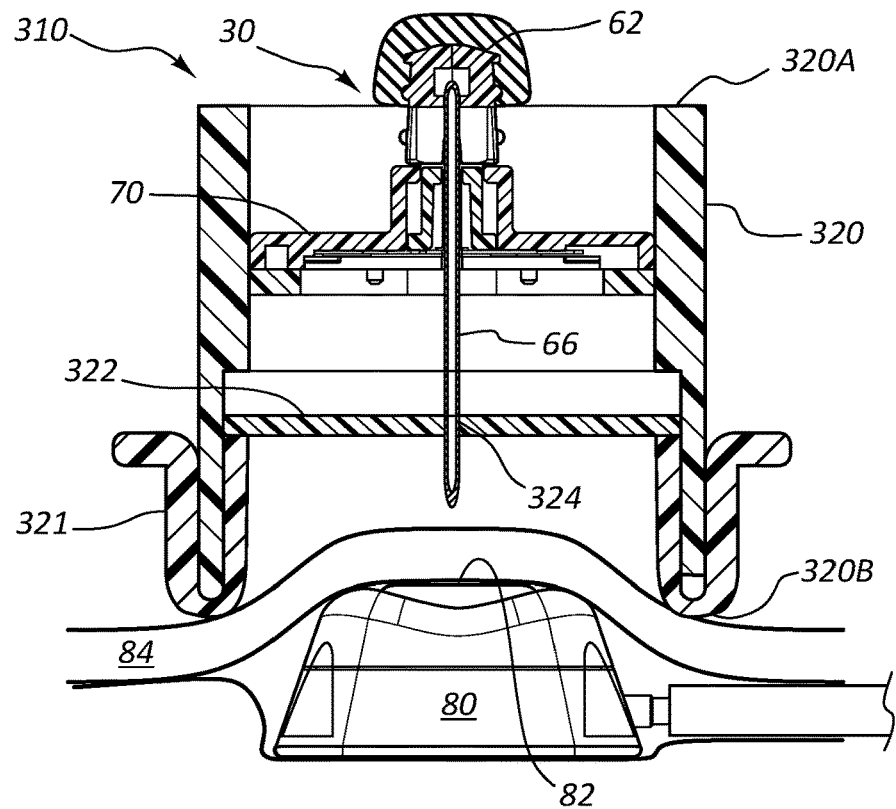
FIG. 7 is a cross-sectional side view of an insertion device according to one embodiment.

FIG. 7 shows a port needle insertion device ("insertion device") 310 according to another embodiment, wherein the insertion device includes a hollow cylindrical body 320 extending between proximal and distal ends 320A, 320B. The needle assembly 30 is supported within the hollow body 320 such that it is slidable to distally advance the needle through a hole 324 defined in a barrier 322, also removably mounted within the hollow body 320. The barrier 322 in the present embodiment includes antimicrobial and hemostatic components, such as a GUARDIVA® dressing, so as to provide antimicrobial/hemostatic effect to the needle 66 when it passes through the hole 324 in the barrier. The barrier 322 can also serve as a needle guide for the needle 66, in one embodiment.

A lower body portion 321 that includes a design similar to that of the insertion device 110 shown in FIG. 5, can be included on the distal end 320B of the body 320 to serve as a stabilization portion for stabilizing the implanted access port 80 when the insertion device 310 is placed over the implanted port. In addition, the body 320 and the barrier 322/hole 324 can serve as a guide portion for guiding the needle along a predetermined path into the septum 82 of the stabilized, implanted access port 80, as desired. The barrier 322 can detach from the insertion device 310 after needle insertion and can remain with the needle assembly 30 as a dressing, in one embodiment. The lower body portion 321 can be made to be removable from the rest of the body 320, in one embodiment.

Figure 8:
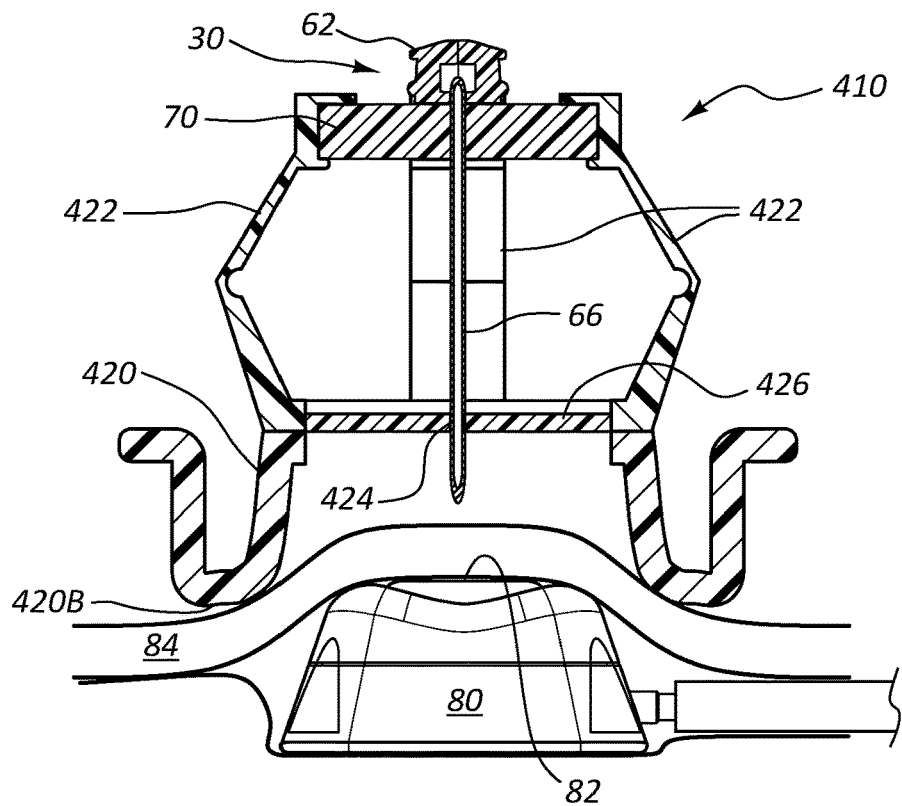
FIG. 8 is a cross-sectional side view of an insertion device according to one embodiment.

FIG. 8 shows a port needle insertion device ("insertion device") 410 according to another embodiment, wherein the insertion device 410 includes a body 420 extending between proximal and distal ends thereof. The body 420 defines a plurality of articulating, living-hinged arms 422 that support the base 70 of the needle assembly 30 at the proximal end of each arm. In the illustrated embodiment, four arms 422 are included on the body 420. The arms 422 are collapsible so as to enable the needle 660 to be distally advanced through a hole 424 in a barrier 426, such as a GUARDIVA® dressing in one embodiment, disposed distal to the arms. As before the barrier 426 can serve as a needle guide, and can be removable to remain with the needle assembly 30 after insertion of the needle 66 into the implanted access port 80.

A distal portion of the body 420 is shaped to define a cavity and serve as a stabilization portion for stabilizing the implanted access port when the insertion device 410 is placed over the implanted port, as shown. The arms 422 (and the barrier 426 in one embodiment) serve as a guide portion for guiding the needle 66 along a predetermined path into the septum 82 of the stabilized, implanted port when the arms 422 are collapsed by user force on the needle hub 62. After needle insertion, the insertion device 410 can be lifted over and removed from the needle assembly 30.

Figure 9:
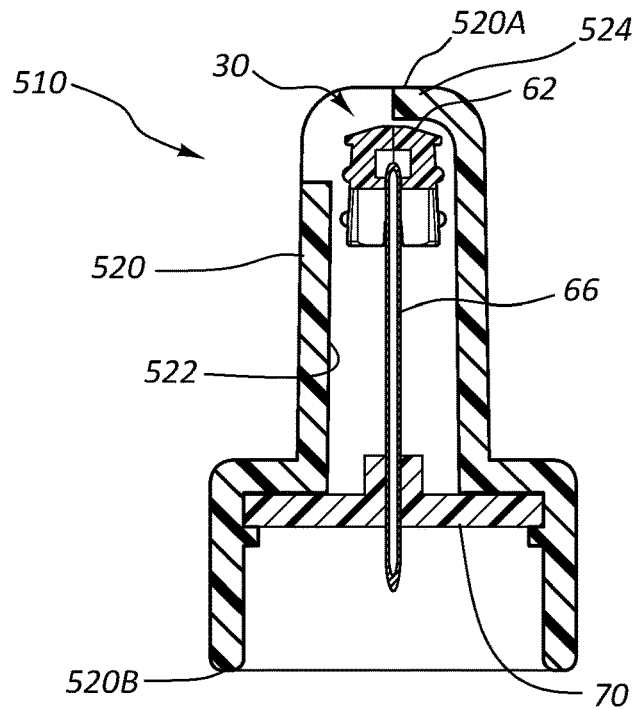
FIG. 9 is a cross-sectional side view of an insertion device according to one embodiment.

FIG. 9 shows a port needle insertion device ("insertion device") 510 according to another embodiment, wherein the insertion device includes a hollow body 520 extending between a proximal end 520A and an annular distal end 520B and defining a cavity 522. The needle assembly 30 is removably disposed within the cavity 522, wherein the needle assembly base 70 is supported by one or more retention surfaces. A guard 524 is provided proximally above a portion of the needle hub 62 so as to prevent unintended proximal pulling of the needle hub, which would prematurely safety the distal tip of the needle 66 within the base 70. A portion of the needle hub 62 is left uncovered so as to enable distal user force to be placed thereon. The needle hub 62 can be pushed by a user to distally advance the distal tip of the needle 66 past the distal end 520B the body 520 and into a subcutaneously implanted access port.

The annular distal end 520B of the insertion device body 520 is shaped to serve as a stabilization portion for stabilizing the implanted access port when the insertion device 510 is placed over the implanted port. Securement of the base 70 within the cavity 522 of the body 520 to enable the needle 66 to be slid relative to the base enables the insertion device 510 to serve as a guide portion for guiding the needle along a predetermined path into the septum of the stabilized, implanted port, as desired. A slot can be provided to enable removal of the insertion device 510 from the needle assembly 30 after insertion of the needle 66.

Figure 10:
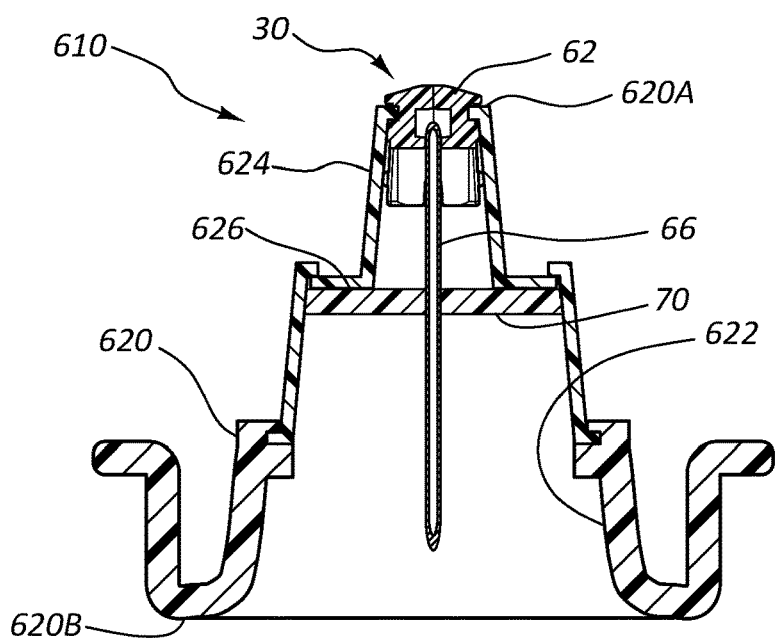
FIG. 10 is a cross-sectional side view of an insertion device according to one embodiment.

FIG. 10 shows a port needle insertion device ("insertion device") 610 according to another embodiment, wherein the insertion device includes a hollow body 620 extending between proximal and distal ends, and further defining a cavity 622. The needle assembly 30 is removably disposed within the cavity 622, wherein the needle assembly base 70 is supported by one or more retention surfaces. The needle hub, base 70, or both components of the needle assembly 30 can be removably secured to a telescoping slide portion 624 that slides with respect to other portions of the body 620 to enable the needle assembly to move distally when user force is applied to the needle hub. Thus, the needle hub 62 can be pushed by a user to distally advance the distal tip of the needle 66 past the distal end of the body 620 and into a subcutaneously implanted access port.

The annular distal end of the insertion device body 620 is shaped to serve as a stabilization portion for stabilizing the implanted access port when the insertion device 610 is placed over the implanted port. Securement of the base 70 and/or needle hub 62 to the slide portion 624 enables the needle 66 to be slid in a distal direction, thus enabling the slide portion 624 to serve as a guide portion for guiding the needle along a predetermined path into the septum of the stabilized, implanted port, as desired. A slot can be provided to enable removal of the insertion device 610 from the needle assembly 30 after insertion of the needle 66.

Figure 11:
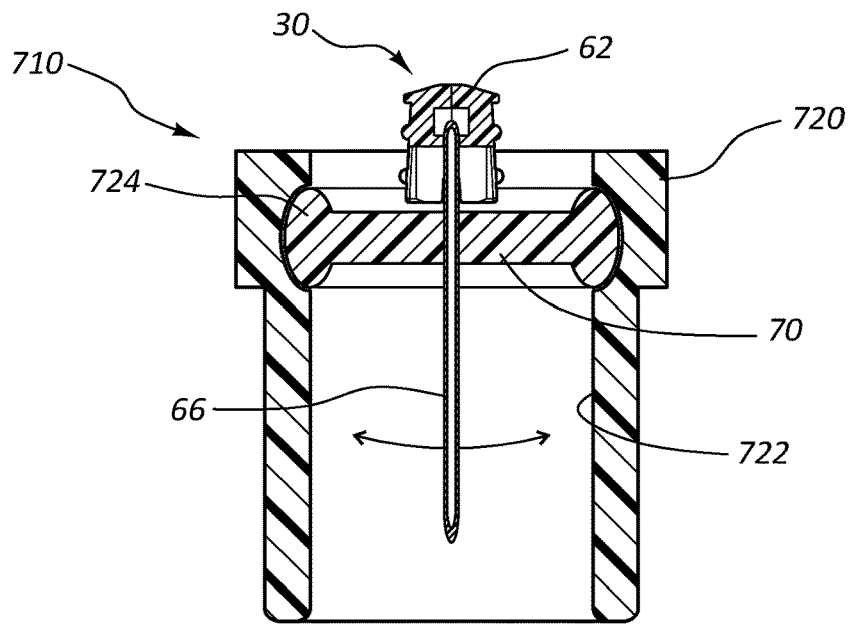
FIG. 11 is a cross-sectional side view of a portion of an insertion device according to one embodiment.

FIG. 11 shows a port needle insertion device ("insertion device") 710 according to another embodiment, wherein the insertion device includes a hollow body 720 extending between proximal and distal ends, and further defining a cavity 722. The needle assembly 30 is removably disposed within a retention feature 724, wherein the needle assembly base 70 is supported by one or more retention surfaces. As shown, the retention feature 724 in the present embodiment supports that base 70 such that the needle assembly can pivot or gimbal about a longitudinal axis of the needle, which enables the needle 66 a limited degree of pivoting ability. This ability for limited pivoting movement in turn prevents the needle 66 from repeatedly impinging upon the same location on the septum of the implanted port, and thus causing possible leakage of the septum, when successive insertion devices 710 are used from time to time to insert a needle into the implanted port. Note that this feature can also be included in other of the insertion device embodiments described herein.

Figure 12:
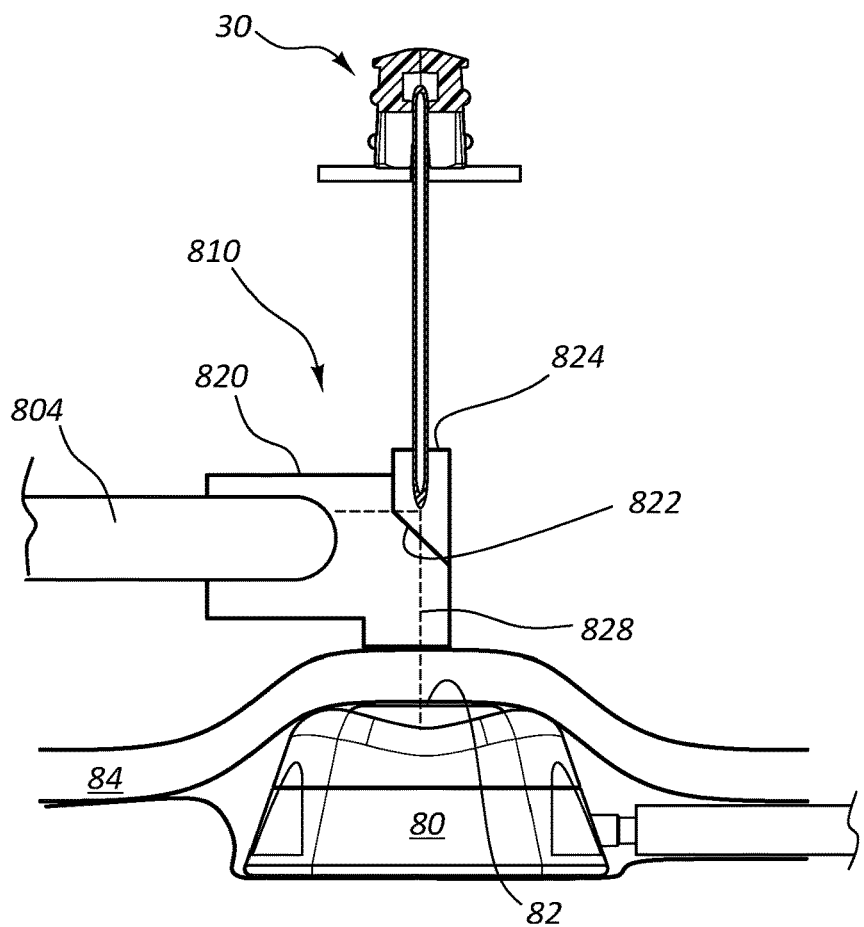
FIG. 12 is a simplified cross-sectional side view of an insertion device according to one embodiment.
Figure 13A:
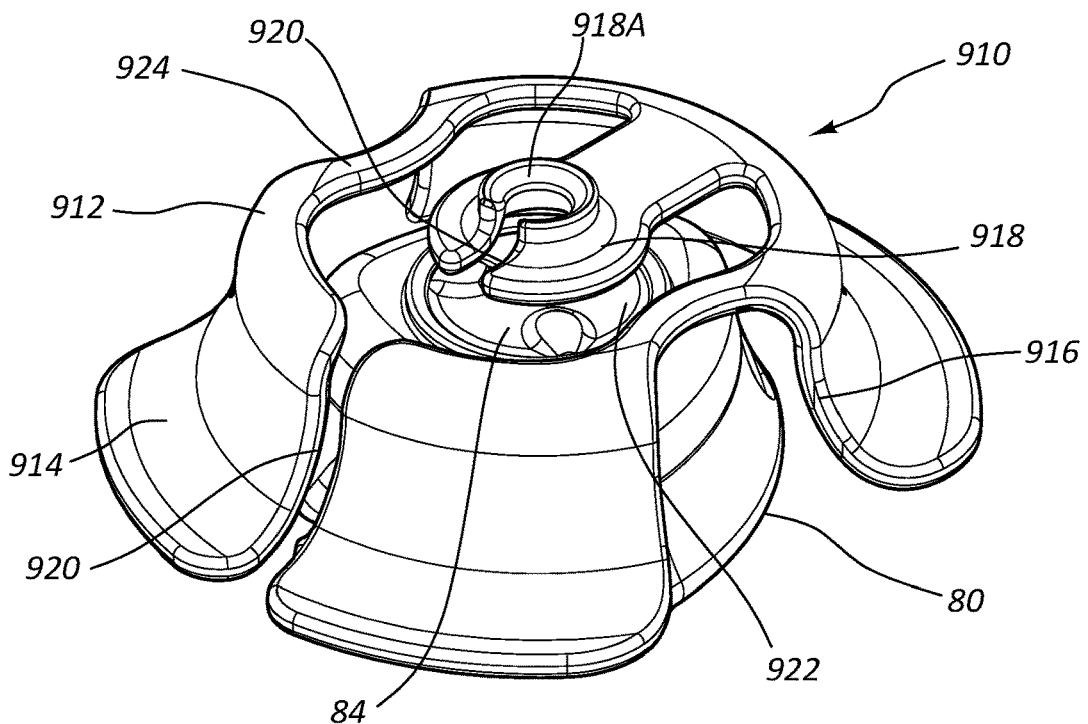
FIGS. 13A-13E are various views of an insertion device according to one embodiment.
Figure 13B:
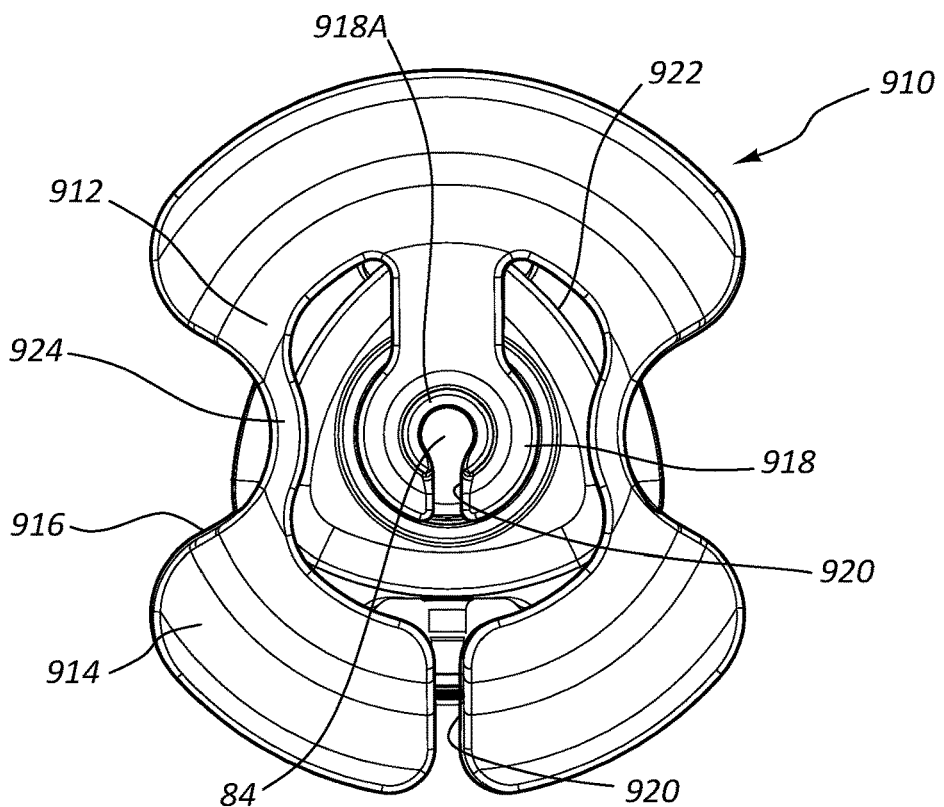
Figure 13C:
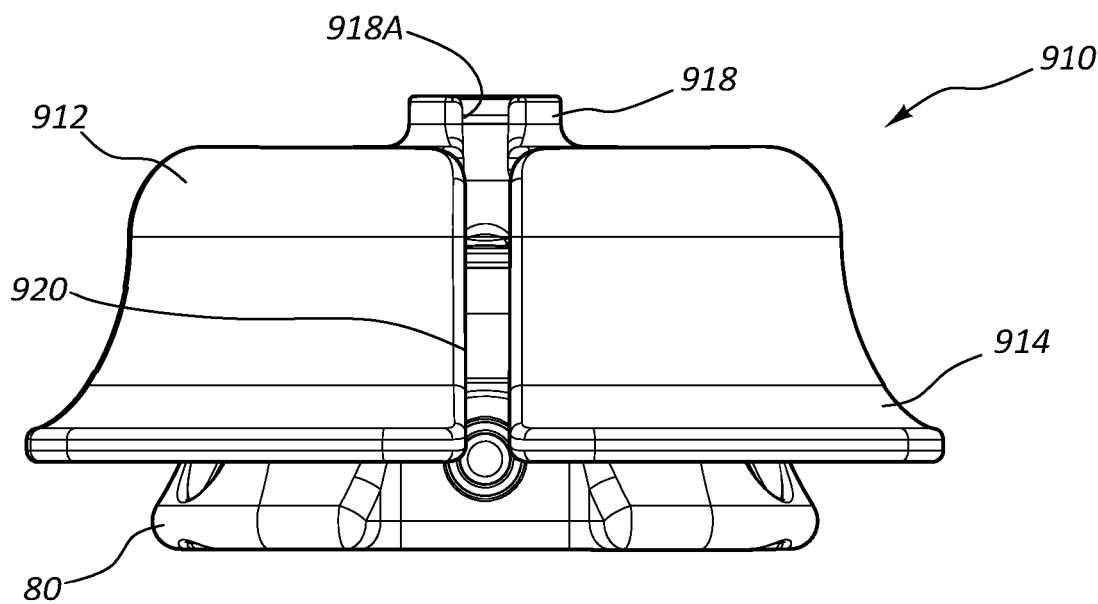
Figure 13D:
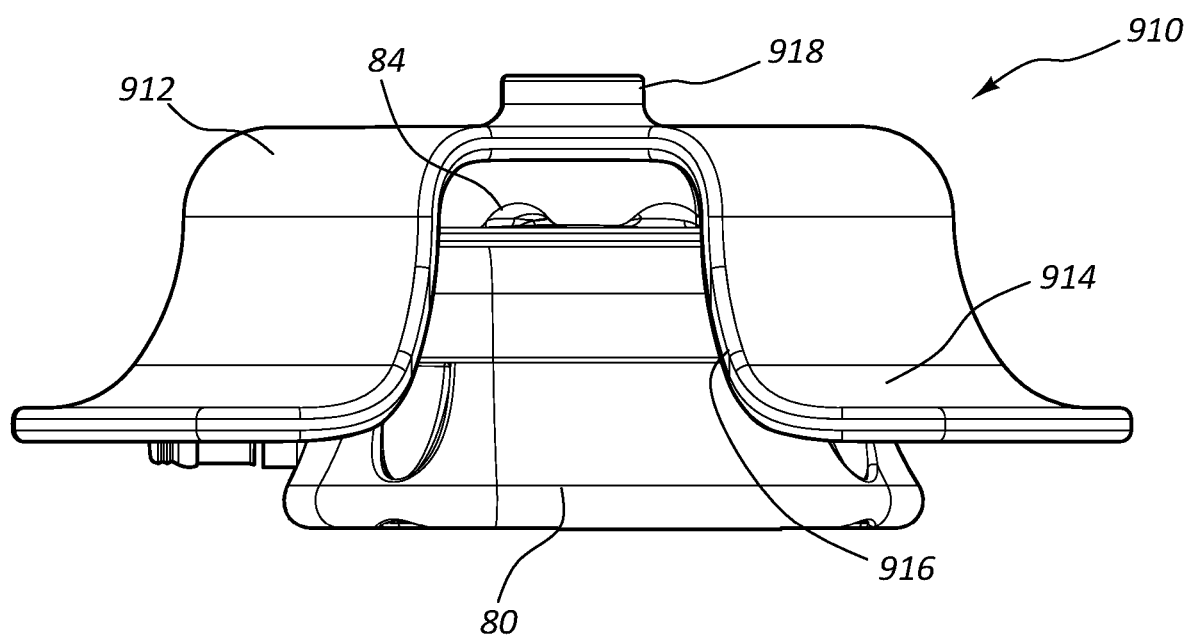
Figure 13E:
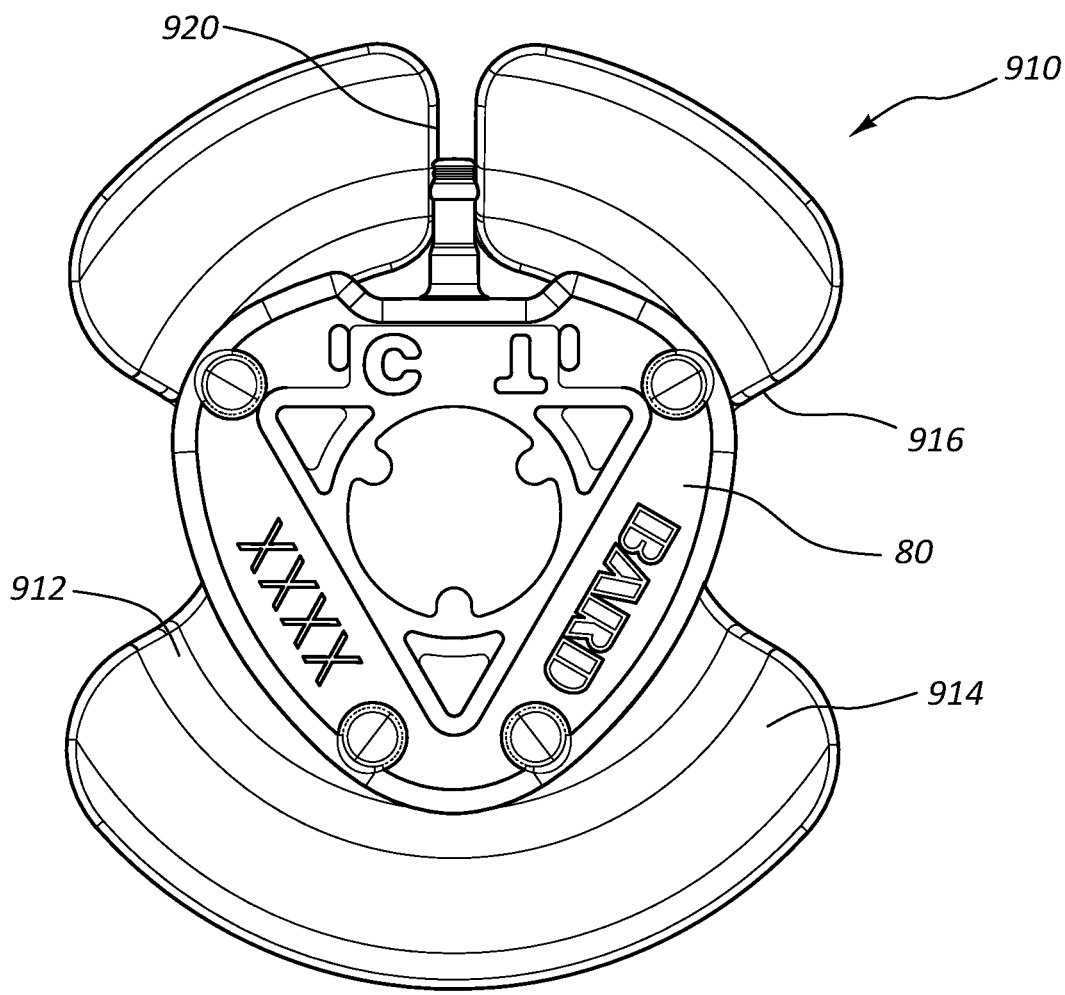

FIG. 12 depicts details of a system for inserting a needle into an implanted access port according to one embodiment, wherein an ultrasound probe 804 is removably received within a body 820 of a port needle insertion device ("insertion device") 810, as shown. The body 820 further includes a reflector surface 822 that is angled to reflect an ultrasound beam 828 from the probe about 90 degrees downward into the implanted access port 80. This configuration enables the probe 804 to be used to ultrasonically image the location of the implanted access port and to pinpoint the septum 82 without the probe being placed in the way of the needle assembly 30. An aperture 824 of the body 820 then enables the needle of the needle assembly 30 to pass the reflector surface 822, extend through the body 820, and enter the implanted port 80.

FIGS. 13A-13E depict an insertion device ("insertion device") 910 for assisting with accessing a subcutaneously implanted access port or other suitable medical device with an infusion or other needle assembly, according to one embodiment. As shown, the insertion device 910 includes a body 912 shaped to sit atop the skin of the patient and generally fit about the access port 80 implanted under the skin. The body 912 includes a lip-like base portion 914 that makes contact with the skin surface, and as such, is smoothly shaped so as to provide patient comfort during use. The body 912 defines a cavity into which the implanted access port 80 and the skin covering the port can be received. The body 912 thus serves as a stabilizing portion in the present embodiment for stabilizing the implanted access port 80 prior to needle insertion. The size of the device cavity can vary from what is shown and described herein.

A pair of finger cutouts 916 is defined by the body 912 to enable the fingers of a user of the insertion device 910 to grasp the skin about the port 80 so as to stabilize its subcutaneous position. The body 912 further includes a needle guide 918 defining a hole 918A suitable for receiving the needle of an infusion or other needle assembly therethrough. The needle guide 918 is positioned so as to guide the needle through the septum 84 of the implanted access port 80 when the device 910 is positioned as shown over the port. The needle guide 918 thus serves as a guide portion in the present embodiment for guiding the needle along a predetermined path into the septum 84 of the access port 80, as desired.

Slots 920 are defined by the device body 912 to enable the device 910 to be removed from about the subcutaneously implanted port 80 once the needle of the needle assembly has been inserted into the port via the hole 918A of the needle guide 918. Indeed, the slots 920 enable the needle of the needle assembly to pass therethrough, thus enabling the device 910 to be slipped out from under the needle assembly after insertion of the needle into the implanted port septum 84. The device body 912 further defines two cutouts 922 about the needle guide 918 that, together with the finger cutouts 916, cooperate to define two living hinges 924. The living hinges 924 are flexible to allow deformation of the device body sufficient to enable the device to be removed from between the skin surface above the implanted port and the inserted needle.

In one embodiment, the guidance device 910 is used by first locating the implanted port 80 under the skin by palpation, then placing the device over the implanted port 80 such that it is received within the cavity defined by the device body 912. The user maintains both the port 80 and the device 910 in place by placing fingers of one hand in the finger cutouts 916 so as to stabilize the port. The other hand of the user can be used to direct the needle of an infusion needle assembly through the needle guide 918, which guides the needle through the skin, down through the septum 84, and into the port reservoir. At this stage, the user can remove the device 910 from the patient by gently pulling on the device body opposite the slots 920 in a lateral direction. The device body 912 will pull past the inserted needle by allowing the needle to pass through the slots 920. The device body 912 will then deform (by virtue of the cutouts 922 and living hinges 924) sufficient to readily pull past the lump of the implanted port 80 and be completely removed.

Note that the slots and cutouts can vary from what is shown and described herein and can be modified according to need in other embodiments. Also, though the insertion device 910 shown and described herein is designed as a universal device to fit over most implanted access ports, the shape, size, and configuration of the insertion device can vary from what is disclosed herein.

The insertion devices described herein can include one or more of a variety of material including metals, metal alloys, thermoplastics (including polypropylene, polycarbonate, and acetyl resin), thermosets, naturally occurring materials, etc.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method for accessing a subcutaneously implanted access port, comprising:

obtaining a needle assembly, including a needle and a needle hub;

positioning an insertion device on a patient over the subcutaneously implanted access port, the insertion device comprising:
- a stabilizing portion defining an open-ended cavity having an outer perimeter designed to circumscribe the subcutaneously implanted access port; and
- a guide portion for guiding the needle along a predetermined path, the guide portion including a retainer component;

attaching the retainer component to the needle hub of the needle assembly;

pressing the stabilizing portion over the subcutaneously implanted access port;

sliding the retainer component in a longitudinal channel of the insertion device; and guiding the needle into the subcutaneously implanted access port.

2. The method according to claim 1, wherein the retainer component includes a first articulating wing and a second articulating wing, each including a tooth that engages a portion of the needle hub to maintain releasable attachment of the retainer component with the needle hub.

3. The method according to claim 2, wherein the longitudinal channel includes a straight proximal portion and an outwardly diverging distal portion, further comprising sliding the retainer component from the straight proximal portion to the outwardly diverging distal portion to open the first articulating wing and the second articulating wing and release engagement of the retainer component with the needle hub.

4. The method according to claim 2, wherein each of the first articulating wing and the second articulating wing includes a pin, wherein the guide portion further includes a first channel and a second channel in which the pin of the respective first articulating wing and second articulating wing is received, each of the first channel and the second channel including a straight proximal portion and an outwardly diverging distal portion, further comprising sliding the retainer component distally to open the first articulating wing and the second articulating wing and release engagement of the retainer component with the needle hub.

5. The method according to claim 1, wherein the guide portion is included with a body of the insertion device, the body including a plurality of articulating arms, a proximal end of each articulating arm removably attaching to a portion of the needle assembly, a distal end being attached to a portion of the body, further comprising collapsing the plurality of articulating arms to guide the needle through a septum of the subcutaneously implanted access port.

6. The method according to claim 1, wherein the guide portion is included with a body of the insertion device, the guide portion including a slide portion slidably disposed with the body, the slide portion releasably retaining the needle assembly, wherein the insertion device includes a needle cover attached to a distal end of the body, further comprising removing the needle cover prior to guiding the needle into the subcutaneously implanted port.

7. The method according to claim 6, wherein the needle assembly is retained by the slide portion such that a distal tip of the needle can pivot about a longitudinal axis of the needle.

8. The method according to claim 1, wherein the insertion device further comprises an antimicrobial barrier disposed in the open-ended cavity.

9. The method according to claim 1, wherein the insertion device further comprises at least one cutout, further comprising deforming the insertion device via the at least one cut out and removing the insertion device from the needle assembly following insertion of the needle into a septum of the subcutaneoulsly implanted access port.

10. The method according to claim 1, wherein the insertion device is formed from a material selected from the group consisting of polypropylene, polycarbonate, and acetyl resin.

11. The method according to claim 1, wherein the insertion device further comprises a removable lower body portion defining the stabilizing portion.

12. The method according to claim 1, wherein the retainer component includes a projection disposed in the longitudinal channel of the insertion device, and wherein the longitudinal channel includes an adjustment zone, further comprising adjusting a length of the longitudinal channel via the adjustment zone.

13. A method for accessing a subcutaneously implanted access port, comprising:

obtaining a needle assembly, including a needle and a needle hub;

positioning an insertion device on a patient over the subcutaneously implanted access port, the insertion device comprising:
- a stabilizing portion defining an open-ended cavity having an outer perimeter designed to circumscribe the subcutaneously implanted access port;
- a pair of first finger cutouts to enable a user to grasp skin of the patient around the subcutaneously implanted access port;
- a first removal slot to enable the insertion device to be removed following insertion of the needle into the subcutaneously implanted access port; and
- a guide portion for guiding the needle, the guide portion including a second removal slot aligned with the first removal slot;

using the pair of first finger cutouts to maintain the subcutaneously implanted access port and the insertion device in place;

guiding the needle into the subcutaneously implanted access port; and removing the insertion device so that the needle passes through the first removal slot and the second removal slot.

14. The method according to claim 13, wherein the insertion device has a shape that resembles the subcutaneously implanted access port.

15. The method according to claim 14, wherein a top surface of the insertion device includes a pair of second finger cutouts that together with the pair of first finger cutouts cooperate to define living hinges, wherein removing the insertion device comprises deformation of the insertion device via the living hinges.

\* \* \* \* \*